(12) United States Patent
Townsend et al.

(10) Patent No.: US 10,130,546 B2
(45) Date of Patent: Nov. 20, 2018

(54) MULTI-ACTIVE-AXIS, NON-EXOSKELETAL REHABILITATION DEVICE

(71) Applicant: Barrett Technology, LLC, Newton, MA (US)

(72) Inventors: William T. Townsend, Weston, MA (US); David Wilkinson, Dedham, MA (US); Alexander Jenko, Newton, MA (US); Julian Leland, Newton, MA (US); Arvind Ananthanarayanan, Newton, MA (US); James Patton, Winnetka, IL (US)

(73) Assignee: Barrett Technology, LLC, Newton, MA (US)

(*) Notice: Subject to any disclaimer, the term of this patent is extended or adjusted under 35 U.S.C. 154(b) by 0 days.

(21) Appl. No.: 14/500,810

(22) Filed: Sep. 29, 2014

(65) Prior Publication Data

US 2016/0367428 A1    Dec. 22, 2016

Related U.S. Application Data

(60) Provisional application No. 61/883,367, filed on Sep. 27, 2013.

(51) Int. Cl.
*A61H 1/02* (2006.01)
*B25J 9/00* (2006.01)
*A61B 34/30* (2016.01)

(52) U.S. Cl.
CPC .......... *A61H 1/0274* (2013.01); *A61B 34/30* (2016.02); *A61H 1/0237* (2013.01);
(Continued)

(58) Field of Classification Search
CPC .......... A61H 1/00; A61H 1/001; A61H 1/003; A61H 1/02; A61H 2001/0207;
(Continued)

(56) References Cited

U.S. PATENT DOCUMENTS 4,629,185 A * 12/1986 Amann .............. A63B 21/0083
                                                                482/113
4,669,451 A *  6/1987 Blauth .................... A61F 5/013
                                                                482/901
(Continued)

FOREIGN PATENT DOCUMENTS

CN          101288620        10/2008
CN          101448467         6/2009
(Continued)

OTHER PUBLICATIONS

Burgar, Charles G. et al., Development of robots for rehabilitation therapy: The Palo Alto VA/Stanford experience, Journal of Rehabilitation Research and Development, 2000, pp. 663-673, vol. 37, No. 6.

*Primary Examiner* — Stephen Holwerda
(74) *Attorney, Agent, or Firm* — Pandiscio & Pandiscio

(57) ABSTRACT

A robotic device for operation in association with an appendage of a user, wherein the appendage of the user has an endpoint, the robotic device including: a base; and a robotic arm attached to the base and having an endpoint, the robotic arm having at least two active degrees of freedom relative to the base and being configured so that when the base is appropriately positioned relative to a user, the reference frame of the robotic device is oriented generally similarly to the reference frame of the user and motions of the endpoint of the appendage of the user are mimicked by motions of the endpoint of the robotic arm.

16 Claims, 11 Drawing Sheets

(52) U.S. Cl.
CPC ............... *A61H 2201/1638* (2013.01); *A61H 2201/1659* (2013.01); *A61H 2201/5007* (2013.01)

(58) Field of Classification Search
CPC .......... A61H 2001/0203; A61H 1/0214; A61H 1/0218; A61H 1/0222; A61H 1/0237; A61H 1/0274; A61H 2201/1638; A61H 2201/1659; A61H 2201/5007; B25J 3/04; B25J 9/0006; B25J 9/0078; B25J 9/02; B25J 9/104; B25J 11/009; A31B 34/30
See application file for complete search history.

(56) References Cited

U.S. PATENT DOCUMENTS

| | | |
|---|---|---|
| 4,903,536 A | 2/1990 | Salisbury, Jr. et al. |
| 5,417,643 A * | 5/1995 | Taylor .................. A61H 1/0274 601/24 |
| 5,466,213 A | 11/1995 | Hogan et al. |
| 6,695,795 B2 | 2/2004 | Knoll |
| 8,012,107 B2 | 9/2011 | Einav et al. |
| 8,317,730 B2 | 11/2012 | Zhang et al. |
| 8,740,794 B2 | 6/2014 | Scott |
| 9,044,630 B1 * | 6/2015 | Lampert ............... A63B 23/035 |
| 2004/0067832 A1 * | 4/2004 | Hassler ................ A61H 1/0281 482/142 |
| 2006/0079817 A1 * | 4/2006 | Dewald .................... A61H 1/02 601/5 |
| 2006/0293617 A1 | 12/2006 | Einav et al. |
| 2008/0010706 A1 * | 1/2008 | Moses ................ A61B 17/1764 600/407 |
| 2008/0161733 A1 | 7/2008 | Einav et al. |
| 2009/0276058 A1 * | 11/2009 | Ueda .................... A61H 1/0274 623/57 |
| 2011/0127390 A1 * | 6/2011 | Brown ..................... A47C 1/03 248/118 |
| 2011/0137464 A1 | 6/2011 | Sabater Navarro et al. |
| 2011/0300994 A1 * | 12/2011 | Verkaaik .............. A61H 1/0274 482/51 |
| 2013/0060171 A1 * | 3/2013 | Fu ........................ A61H 1/0274 601/5 |
| 2014/0016803 A1 | 1/2014 | Puskarich |
| 2014/0277726 A1 | 9/2014 | Nakamura et al. |
| 2014/0309779 A1 | 10/2014 | Niu |

FOREIGN PATENT DOCUMENTS

| | | |
|---|---|---|
| CN | 102283761 | 12/2011 |
| JP | 3-73133 | 7/1991 |
| WO | WO 2008/047355 | 4/2008 |
| WO | WO 2015/048688 | 4/2015 |
| WO | WO 2015/087335 | 6/2015 |

\* cited by examiner

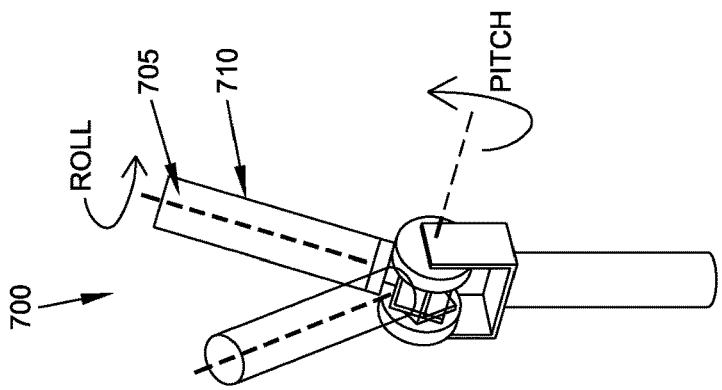

FIG. 8C

WAM Differential-Pitch-Roll
ROLL ARROW: DIFFERENTIAL OUTPUT AXIS ROTATION
PITCH ARROW: DIFFERENTIAL INPUT AXIS ROTATION

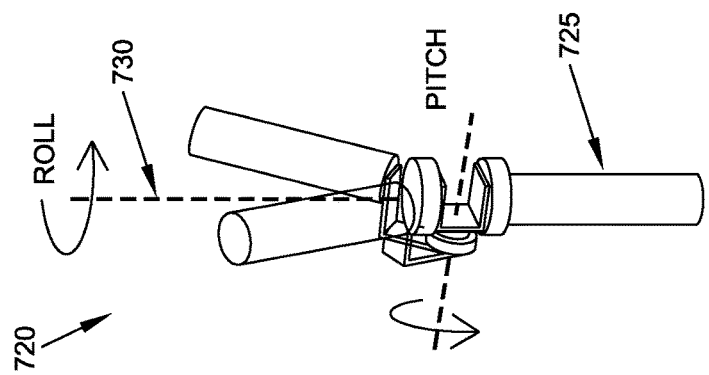

FIG. 8B

Wrist Differential-Roll-Pitch
PITCH ARROW: DIFFERENTIAL OUTPUT AXIS ROTATION
ROLL ARROW: DIFFERENTIAL INPUT AXIS ROTATION

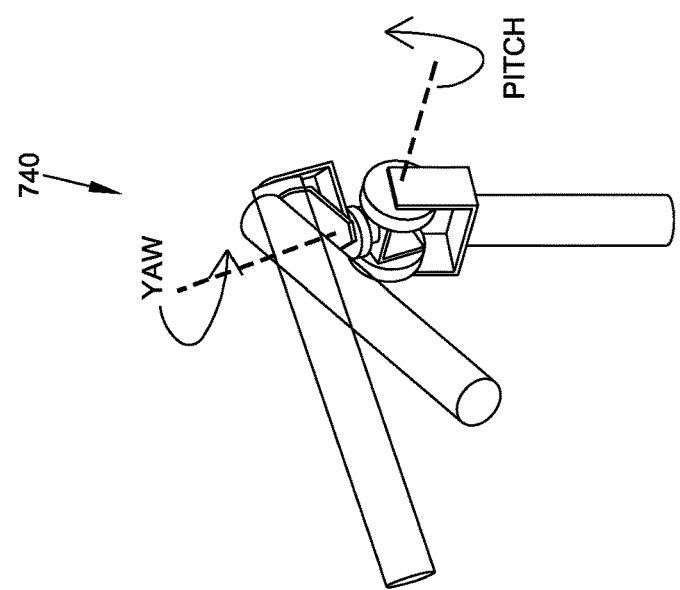

FIG. 8A

Rehab Differential-Pitch-Yaw
YAW ARROW: DIFFERENTIAL OUTPUT AXIS ROTATION
PITCH ARROW: DIFFERENTIAL INPUT AXIS ROTATION

MULTI-ACTIVE-AXIS, NON-EXOSKELETAL REHABILITATION DEVICE

REFERENCE TO PENDING PRIOR PATENT APPLICATION

This patent application claims benefit of prior U.S. Provisional Patent Application Ser. No. 61/883,367, filed Sep. 27, 2013 by Barrett Technology, Inc. and William T. Townsend et al. for THREE-ACTIVE-AXIS REHABILITATION DEVICE, which patent application is hereby incorporated herein by reference.

STATEMENT REGARDING FEDERALLY SPONSORED RESEARCH OR DEVELOPMENT

This invention was made with Government support under Agreement No. HR0011-12-9-0012 awarded by DARPA. The Government has certain rights in the invention.

FIELD OF THE INVENTION

This invention relates to devices for the rehabilitation of disabled or otherwise impaired anatomical extremities.

BACKGROUND OF THE INVENTION

A new and exciting branch of physical and occupational therapies is therapy assisted by a computer-directed robotic arm or device (also called a "manipulator" to distinguish it from the human arm that may engage it, in certain embodiments). The potential benefits of using a manipulator system for tasks such as post-stroke rehabilitative therapy, which typically involves moving a patient's limb(s) through a series of repeated motions, are significant. There exist some types of therapy, such as error-augmentation therapy, that simply cannot be implemented effectively by a human therapist. Furthermore, computer-directed therapy can engage the patient in games, thereby making the experience more enjoyable and encouraging longer and more intense therapy sessions, which are known to benefit patients. Finally, the therapist is able to work with more patients, and is able to offer patients increased therapy duration since the session is no longer constrained by the therapist's physical endurance.

A useful way to categorize robotic rehabilitation systems is by the number of degrees of freedom, or DOFs, that they have. The majority of commercial robotic rehabilitation systems fall into one of two broad categories: low-DOF (typically one to three DOFs) systems which are positioned in front of the patient, and high-DOF (typically six or more DOFs) exoskeleton systems, which are wrapped around the patient's limb, typically an arm or leg. The current approaches for both categories exhibit significant shortcomings, which has contributed to limited realization of the potential of robotic rehabilitation therapies.

Low-DOF systems are usually less expensive than high-DOF systems, but they also typically have a smaller range of motion. Some, such as the INMOTION ARM™ Therapy System of Interactive Motion Technologies of Watertown, Mass., USA, or the KINARM END-POINT ROBOT™ system of BKIN Technologies of Kingston, Ontario, Canada, are limited to only planar movements, greatly reducing the number of rehabilitation tasks that they can be used for. Those low-DOF systems which are not limited to planar movements must typically contend with issues such as avoiding blocking a patient's line of sight, like the DEXTREME™ system of BioXtreme of Rehovot, Israel; providing an extremely limited range of motion, such as with the REOGO® system of Motorika Medical Ltd of Mount Laurel, N.J., USA; and insufficiently supporting a patient's limb. Most of these systems occupy space in front of the patient, impinging on the patient's workspace, increasing the overall footprint needed for a single rehabilitation "station" and consuming valuable space within rehabilitation clinics.

Meanwhile, high-DOF exoskeletal systems, such as the ARMEO® Power system of Hocoma AG of Volketswil, Switzerland, the ARMEO® Spring Spring system of Hocoma AG of Volketswil, Switzerland, and the 8+2 DOF exoskeletal rehabilitation system disclosed in U.S. Pat. No. 8,317,730, are much more complex and consequently generally more expensive than comparable low-DOF systems. While such high-DOF exoskeletal systems usually offer larger ranges of motion than low-DOF systems, their mechanical complexity also makes them bulky, and they typically wrap around the patient's limb, making the systems feel threatening and uncomfortable to patients. Furthermore, human joints do not conform to axes separated by links the way robots do, and the anatomy of every human is different, with different bone lengths and different joint geometries. Even with the high number of axes present in high-DOF systems, fine-tuning an exoskeleton system's joint locations and link lengths to match that of the patient takes considerable time, and even then the system frequently over-constrains the human's limb, potentially causing more harm than good.

Finally, there are a handful of currently available devices which do not fit in either of the two categories listed above: for example, high-DOF non-exoskeletal devices, or low-DOF exoskeletal devices. To date, these devices have generally suffered the weaknesses of both categories, without leveraging the strengths of either. A particularly notable example is the KINARM EXOSKELETON ROBOT™ of BKIN Technologies of Kingston, Ontario, Canada, which is an exoskeletal rehabilitation device designed for bimanual and unimanual upper-extremity rehabilitation and experimentation in humans and non-human primates. Like the KINARM END-POINT ROBOT™ of BKIN Technologies of Kingston, Ontario, Canada, the KINARM EXOSKELETAL ROBOT™ system provides only two degrees of freedom for each limb, limiting the range of rehabilitation exercises that it can conduct. Meanwhile, by implementing an exoskeletal design, the KINARM EXOSKELETAL ROBOT™ device can provide some additional support to the patient's limb, but at the cost of significant increases in device size, cost, complexity and set-up time.

While robot-assisted physical and occupational therapy offers tremendous promise to many groups of patients, the prior art has yet to match that promise. As the previous examples have shown, current therapy devices are either too simplistic and limited, allowing only the most rudimentary exercises and frequently interfering with the patient in the process; or too complex and cumbersome, making the devices expensive, intimidating to patients, and difficult for therapists to use. Thus, there remains a need for a novel device and method that can provide patients and therapists with the ability to perform sophisticated 2-D and 3-D rehabilitation exercises, in a simple, unobtrusive and welcoming form factor, at a relatively low price.

SUMMARY OF THE INVENTION

The present invention bridges the categories of low-DOF and high-DOF rehabilitation devices, offering the usability, mechanical simplicity and corresponding affordability of a low-DOF system, as well as the reduced footprint, range of motion, and improved support ability of a high-DOF system. The present invention comprises a relatively low number of active (powered) DOFs—in the preferred embodiment, three active DOFs, although the novel features of the invention can be implemented in systems with other numbers of DOFs—which reduces the device's cost and complexity well below that of high-DOF exoskeletal systems. However, because of the innovative positional and orientational relationship of the system to the patient—unique among non-exoskeletal systems to date, as explained further below—the device of the present invention enjoys advantages that have previously been limited to high-DOF exoskeletal systems, such as more optimal torque-position relationships, better workspace overlap with the patient and a larger range of motion. In addition, it has been discovered that a novel implementation of a cabled differential (with the differential input being used as a pitch axis and the differential output being used as a yaw axis relative to the distal links of the device) permits the mass and bulk of the power drives (e.g., motors) to be shifted to the base of the system, away from the patient's workspace and view. Through the combination of these two major innovations—the orientation and position of the device relative to the patient, and the implementation of a cabled differential with special kinematics—as well as other innovations, the present invention provides a unique rehabilitation device that fills a need in the rehabilitation market, and is capable of a wide variety of rehabilitation tasks. Significantly, the present invention enables a new method for bimanual rehabilitation—a new class of rehabilitative therapy where multiple limbs, usually arms, are rehabilitated simultaneously—in which rehabilitative exercises can be conducted in three dimensions, by using two similar devices, simultaneously and in a coordinated fashion, on two different limbs of the patient.

In one preferred form of the invention, there is provided a non-exoskeletal rehabilitation device, with as few as 2 active degrees of freedom, wherein the device is oriented and positioned such that its reference frame is oriented generally similarly to that of the patient, and motions of the patient's endpoint are mimicked by motions of the device's endpoint.

In another preferred form of the invention, there is provided a non-exoskeletal rehabilitation device, with as few as 2 active degrees of freedom, of which 2 degrees are linked through a cabled differential.

In another preferred form of the invention, there is provided a method in which a rehabilitation device that is designed to be capable of inducing motion in three or more degrees of freedom, easily reconfigurable to allow both right-handed and left-handed usage, and located relative to the patient such that two devices may be used simultaneously without interfering with each other, is paired bidirectionally with a second similar device and used for bimanual rehabilitation.

In another preferred form of the invention, there is provided a robotic device for operation in association with an appendage of a user, wherein the appendage of the user has an endpoint, the robotic device comprising:
  a base; and
  a robotic arm attached to the base and having an endpoint, the robotic arm having at least two active degrees of freedom relative to the base and being configured so that when the base is appropriately positioned relative to a user, the reference frame of the robotic device is oriented generally similarly to the reference frame of the user and motions of the endpoint of the appendage of the user are mimicked by motions of the endpoint of the robotic arm.

In another preferred form of the invention, there is provided a method for operating a robotic device in association with an appendage of a user, wherein the appendage of the user has an endpoint, the method comprising:
  providing a robotic device comprising:
  a base; and
  a robotic arm attached to the base and having an endpoint, the robotic arm having at least two active degrees of freedom relative to the base and being configured so that when the base is appropriately positioned relative to a user, the reference frame of the robotic device is oriented generally similarly to the reference frame of the user and motions of the endpoint of the appendage of the user are mimicked by motions of the endpoint of the robotic arm;
  positioning the base relative to the user so that the reference frame of the robotic device is oriented generally similarly to the reference frame of the user, and attaching the appendage of the user to the robotic arm; and
  moving at least one of the endpoint of the appendage of the user and the endpoint of the robotic arm.

BRIEF DESCRIPTION OF DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 8A, 8B and 8C are schematic views showing the pitch-yaw configuration of the robotic device of FIGS. 1 and 2 in comparison to the roll-pitch and pitch-roll configurations of prior art devices;

DETAILED DESCRIPTION OF THE PREFERRED EMBODIMENTS

Figure 1:
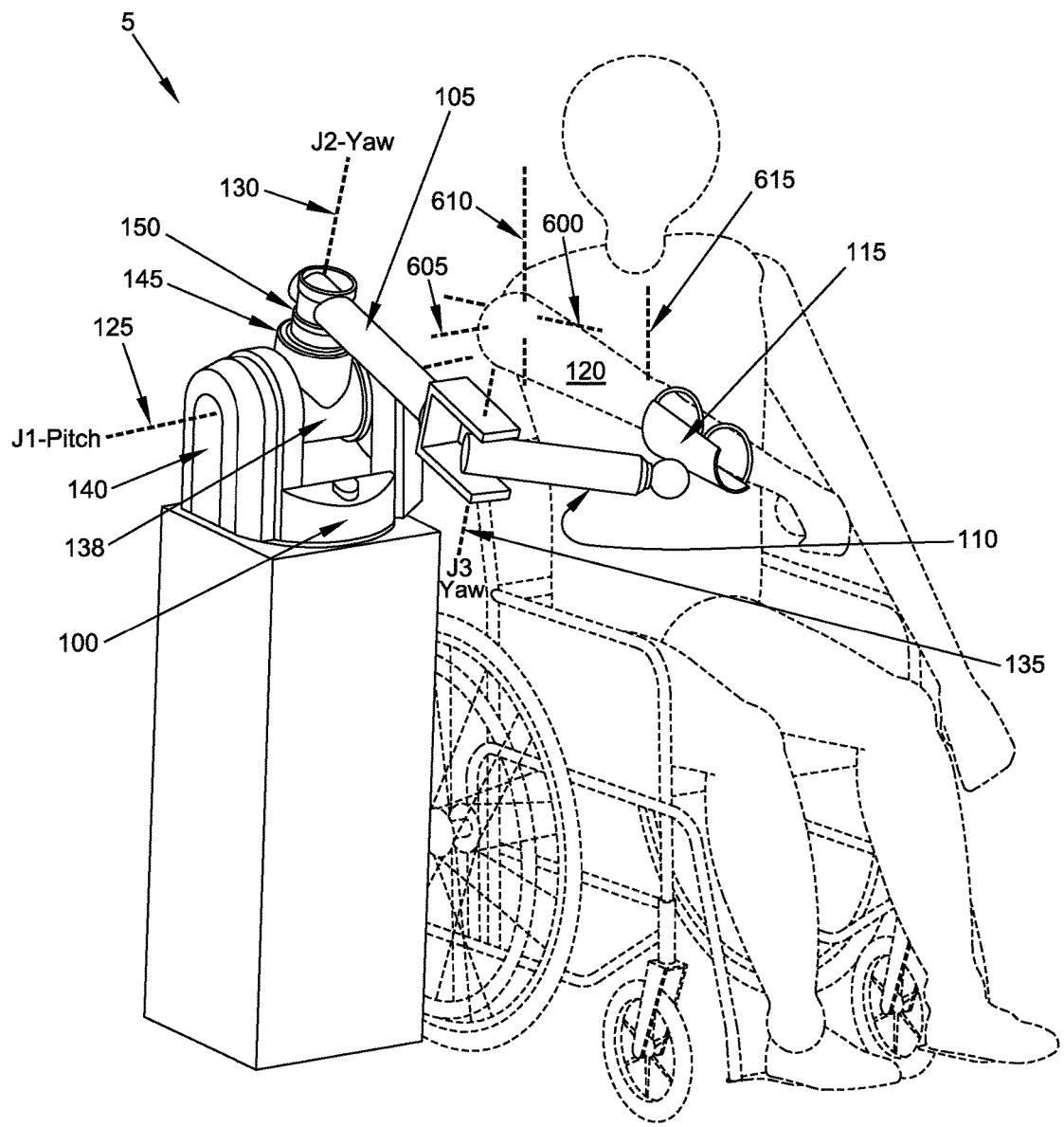
FIGS. 1 and 2 are schematic front perspective views showing one preferred form of robotic device formed in accordance with the present invention.

Looking first at FIG. 1, there is shown a novel multi-active-axis, non-exoskeletal robotic device 5 that is suitable for various robotic-assisted therapies and other applications. Robotic device 5 generally comprises a base 100, an inner link 105, an outer link 110, and a coupling element 115 for coupling outer link 110 to a patient, commonly to a limb of the patient (e.g., as shown in FIG. 1, the patient's arm 120).

The preferred embodiment shown in FIG. 1 has three degrees of freedom, although it will be appreciated by one skilled in the art that the present invention may comprise fewer or greater numbers of degrees of freedom. Three degrees of freedom theoretically provide the ability to access all positions in Cartesian space, subject to the kinematic limitations of the device, such as joint limits, link lengths, and transmission ranges. To produce those three degrees of freedom, robotic device 5 comprises three revolute joints, shown in FIG. 1 as joint J1 providing pitch around an axis 125, joint J2 providing yaw around an axis 130 and joint J3 providing yaw around an axis 135. In the preferred embodiment, these joints are implemented as follows. Joint J1 is a pitch joint, and consists of a segment 138 which rotates inside a generally U-shaped frame 140. Joint J2 is a yaw joint, and consists of a second segment 145 attached perpendicularly to segment 138. This segment 145 contains a third segment 150, which rotates inside segment 145. In the preferred embodiment, these two joints (i.e., joint J1 and joint J2) are linked through a cabled differential as will hereinafter be discussed. Joint J3 is also a yaw joint, and is separated from joint J2 by inner link 105. As will hereinafter be discussed, a cable transmission connects the motor that actuates joint J3 (and which is located coaxially to the axis 130 of joint J2, as will hereinafter be discussed) to the output of joint J3; this cable transmission runs through inner link 105. It should be noted that while this particular embodiment has been found to be preferable, the present invention may also be implemented in alternative embodiments including but not limited to:

devices with alternative kinematics—for example, three joints in a yaw-pitch-yaw arrangement;

devices using other types of joints, such as prismatic joints; and devices that implement other drive technologies, such as gear drivetrains, belts, hydraulic drives, etc.

To provide additional degrees of freedom, different endpoint attachments may be provided at the location of the coupling element 115, to permit different degrees of control over the patient's limb orientation, or to provide additional therapeutic modalities. By way of example but not limitation, different endpoint attachments may comprise a single-DOF endpoint attachment for performing linear rehabilitation exercises; or a three-DOF endpoint attachment to enable more complex motions, by enabling control over the orientation of the patient's limb; or a actively-controlled multi-DOF endpoint attachment. By reducing the number of degrees of freedom in the core of the robotic device to three in the preferred implementation (i.e., the robotic device 5 shown in FIG. 1), the design of the robotic device is vastly simplified, reducing cost while maintaining the device's ability to provide a wide range of rehabilitative services including three-dimensional rehabilitative therapies.

Figure 6:
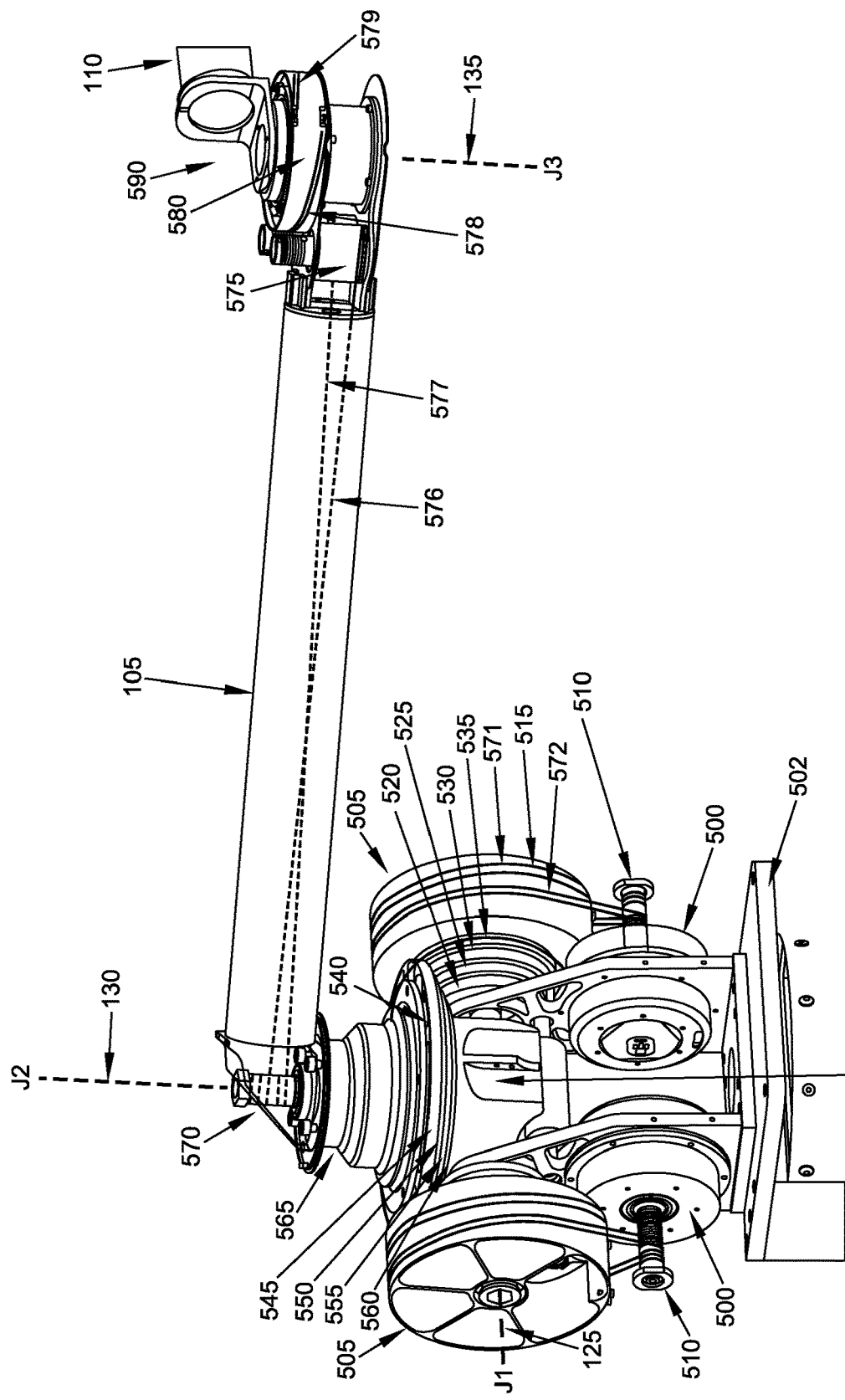
FIGS. 6 and 7 are schematic views showing details of selected portions of the robotic device of FIGS. 1 and 2.

Looking next at FIGS. 1 and 6, further details of the construction of the preferred embodiment of the present invention are shown. The preferred embodiment of the robotic device consists of the following four kinematic frames:

1) The ground kinematic frame, consisting of all components that are generally static when the device is in use;
2) The joint J1 kinematic frame, consisting of all non-transmission components that rotate exclusively about the axis 125 of joint J1;
3) The joint J2 kinematic frame, consisting of all non-transmission components that may rotate exclusively about the axis 125 of joint J1 and the axis 130 of joint J2;
4) The joint J3 kinematic frame, consisting of all non-transmission components that may rotate about the axis 125 of joint J1, the axis 130 of joint J2 and the axis 135 of joint J3.

In this definition of kinematic frames, transmission components are excluded to simplify definition: a pulley within a transmission may be located away from a given joint, but rotate with that joint. Similarly, some pulleys in the system may be caused to rotate by the motion of more than one axis—for example, when they are part of a cabled differential, such as is employed in the preferred form of the present invention.

In the preferred embodiment, joints J1 and J2 are implemented through the use of a cabled differential transmission, designed similarly to that disclosed in U.S. Pat. No. 4,903,536, which patent is hereby incorporated herein by reference.

As described in U.S. Pat. No. 4,903,536, a cabled differential is a novel implementation of a differential transmission, in which two input pulleys (e.g., pulleys 505 in the robotic device 5 shown in FIG. 6) with a common axis of rotation are coupled to a third common output pulley, (e.g., pulley 540 in the robotic device 5 shown in FIGS. 1 and 6) which is affixed to a spider or carrier (e.g., in carrier 541 in the robotic device 5 shown in FIGS. 1 and 6). This carrier is able to rotate about the common axis of rotation of the two input pulleys independently of those pulleys. The output pulley, meanwhile, is able to rotate about an axis perpendicular to, and coincident with, the common axis of rotation. The two input pulleys are coupled to the output pulley such that a differential relationship is established between the three, wherein the rotation of the output pulley (e.g., pulley 540 in robotic device 5) is proportional to the sum of the rotations of the two input pulleys (e.g., pulleys 505 in robotic device 5), and the rotation of the carrier (e.g., carrier 541 in robotic device 5) is proportional to the difference of the rotations of the two input pulleys. In a robotic system, the rotation of the carrier of the differential is used to produce motion of the system about one axis of rotation (in the preferred embodiment, about the axis 125 of joint J1), and the rotation of the output of the differential transmission (i.e., the rotation of output pulley 540) is used to produce motion of the system about a second axis of rotation (in the preferred embodiment, about the axis 130 of joint J2). The use of a cabled differential enables these two motions to be produced by motors which are affixed to lower kinematic frames (in the case of the preferred embodiment, to the ground kinematic frame). This dramatically decreases the moving mass of the device, thereby improving the dynamic performance and feel of the device. In the preferred implementation, this transmission consists of two motors 500, input pulleys 505, output pulley 540, etc., as hereinafter discussed.

Stated another way, as described in U.S. Pat. No. 4,903,536, the cabled differential is a novel implementation of a differential transmission, in which two input pulleys (e.g., pulleys 505 in robotic device 5) with a common axis of rotation are coupled to a third common output pulley (e.g., pulley 540 in robotic device 5), which rotates about an axis perpendicular to the input pulley axis, and is affixed to a carrier (e.g., carrier 541 in robotic device 5) that rotates about the input pulley axis. The two input pulleys are coupled to the output pulley such that a differential relationship is established between the three, wherein the rotation of the output pulley is proportional to the sum of the rotations of the two input pulleys, and the rotation of the carrier is proportional to the difference of the rotations of the two input pulleys. This mechanism produces rotations about two axes (e.g., axis 125 of joint J1 and axis 130 of joint J2), while allowing the motors producing those motions to be affixed to lower kinematic frames, thereby decreasing the moving mass of the device and improving dynamic performance and feel. In the preferred implementation, this transmission consists of two motors 500, input pulleys 505, output pulley 540, etc., as hereinafter discussed.

In other words, as described in U.S. Pat. No. 4,903,536, the cabled transmission is a novel implementation of a differential transmission, wherein two input pulleys (e.g., pulleys 505) are connected to a third common output pulley (e.g., pulley 540) such that the rotation of the output pulley is proportional to the sum of the rotations of the two input pulleys, and the rotation of the differential carrier (e.g., carrier 541) is proportional to the difference of the rotations of the two input pulleys. In the preferred implementation, this transmission consists of two motors 500, input pulleys 505, output pulley 540, etc., as hereinafter discussed.

As seen in FIG. 6, the cabled transmission preferably comprises two motors 500 which are affixed to the ground kinematic frame (e.g., base 502), which are coupled to input pulleys 505, through lengths of cable 571 and 572—commonly wire rope, but alternatively natural fiber, synthetic fiber, or some other construction generally recognized as a form of cable—that are attached to the pinions 510 of the motors 500, wrapped in opposite directions but with the same chirality about pinions 510, and terminated on the outer diameters 515 of the input pulleys 505. These input pulleys 505 rotate about the axis 125 of joint J1, but their rotation may produce rotation of the device about the axis 125 of joint J1, the axis 130 of joint J2, or both axes simultaneously, due to the properties of the cable differential; furthermore, these input pulleys 505 are fixed to neither the aforementioned joint J1 kinematic frame nor the aforementioned joint J2 kinematic frame. As per U.S. Pat. No. 4,903,536, these input pulleys 505 include both large outer diameters 515, as well as a series of substantially smaller stepped outer diameters 520, 525, 530 and 535. These smaller stepped outer diameters 520, 525, 530 and 535 are coupled through further lengths of cable to an output pulley 540, which comprises a series of stepped outer diameters 545, 550, 555, and 560, which are substantially larger than the steps 520, 525, 530 and 535 they are coupled to on input pulleys 505. This output pulley 540 rotates about the axis 130 of joint J2, and is fixed to the joint J2 kinematic frame. It has been found that it can be useful to make the range of motion of joint J2 symmetric about a plane coincident with joint J2 and perpendicular to joint J1, as this facilitates switching the device's chirality as described below.

By implementing this set of diametral relationships in the series of pulleys, (i.e., input pulleys 505 and output pulley 540) progressively higher transmission ratios are achieved through the cabled transmission. In the preferred embodiment, a transmission ratio of 8.51 is implemented between the motor pinions 510 and input pulleys 505, and a transmission ratio of 1.79 is implemented between the input pulleys 505 and the output pulley 540, generating a maximum transmission ratio between the motor pinions 510 and output pulley 540 of 15.26. Throughout this cabled transmission, and all cabled transmissions of the present invention, care is taken to ensure that the ratio between the diameter of a given cable and the smallest diameter that it bends over is kept at 1:15 or smaller. Larger ratios, occurring when the cable is bent over smaller diameters, are known to significantly reduce cable fatigue life.

Still looking now at FIG. 6, distal to the output pulley 540 is another cable transmission, comprising a motor 565, coupled from its motor pinion 570 through cables 576, 577 to intermediate pulleys 575, which are in turn coupled through cables 578, 579 to an output pulley 580. These transmission cables are contained inside the inner link 105, which is fixed to the aforementioned joint J2 kinematic frame. In this additional transmission, no differential element is implemented. In keeping with the cable transmission design taught in U.S. Pat. No. 4,903,536, the first stage of the cable transmission between the motor pinion 570 and intermediate pulleys 575 is designed to be a high-speed, lower-tension transmission stage that traverses a greater distance; while the second stage of the cable transmission, between the intermediate pulleys 575 and the output pulley 580, is designed to be a low-speed, higher-tension transmission stage that traverses a very short distance. In this transmission, the intermediate pulleys 575, output pulley 580 and the joint axis 135 of joint J3 are substantially distal to the motor 565, a design which is accomplished by implementing a long cable run between motor pinion 570 and intermediate pulleys 575.

As described in U.S. Pat. No. 4,903,536, this design has the benefit of moving the mass of the motor 565 towards the base of the robotic device, reducing the inertia of the system. In the preferred implementation, the motor's mass is positioned coaxial to the axis 130 of joint J2, and as close as possible to the axis 125 of joint J1, thereby reducing inertia about both axes. This design is particularly valuable in the preferred implementation shown, since the mass of motor 565 is moved close to both the axis 130 of joint J2 and the axis 125 of joint J1, thereby reducing inertia about both axes. A transmission ratio of 1.89 is preferably implemented between the motor pinion 570 and the intermediate pulleys 575, and a transmission ration of 5.06 is preferably implemented between the intermediate pulleys 575 and the output pulley 580, yielding a maximum transmission ratio between the motor pinion 575 and output pulley 580 of 9.55.

All transmission ratios listed here have been optimized based on a range of factors, including:
  device link lengths;
  device component inertias and moments about axes;
  the intended position of the device relative to the patient;
  motor instantaneous peak and sustained torque limits;
  motor controller output current capacity, and motor current capacity;
  desired ability of device to overpower patient/be overpowered by patient; and
  expected peak output force of patient.

This optimization process is extensive and at least partially qualitative; it is not reproduced here, since both the process and its outcome will change significantly as the above factors change. Based on data gathered from a number of sources and internal experimentation, these forces are estimated to be:
  push/pull away from/towards patient's body: 45 N
  up/down in front of patient: 15 N
  left/right laterally in front of patient: 17 N It should be noted that generous factors of safety have been applied to these estimates.

Figure 7:
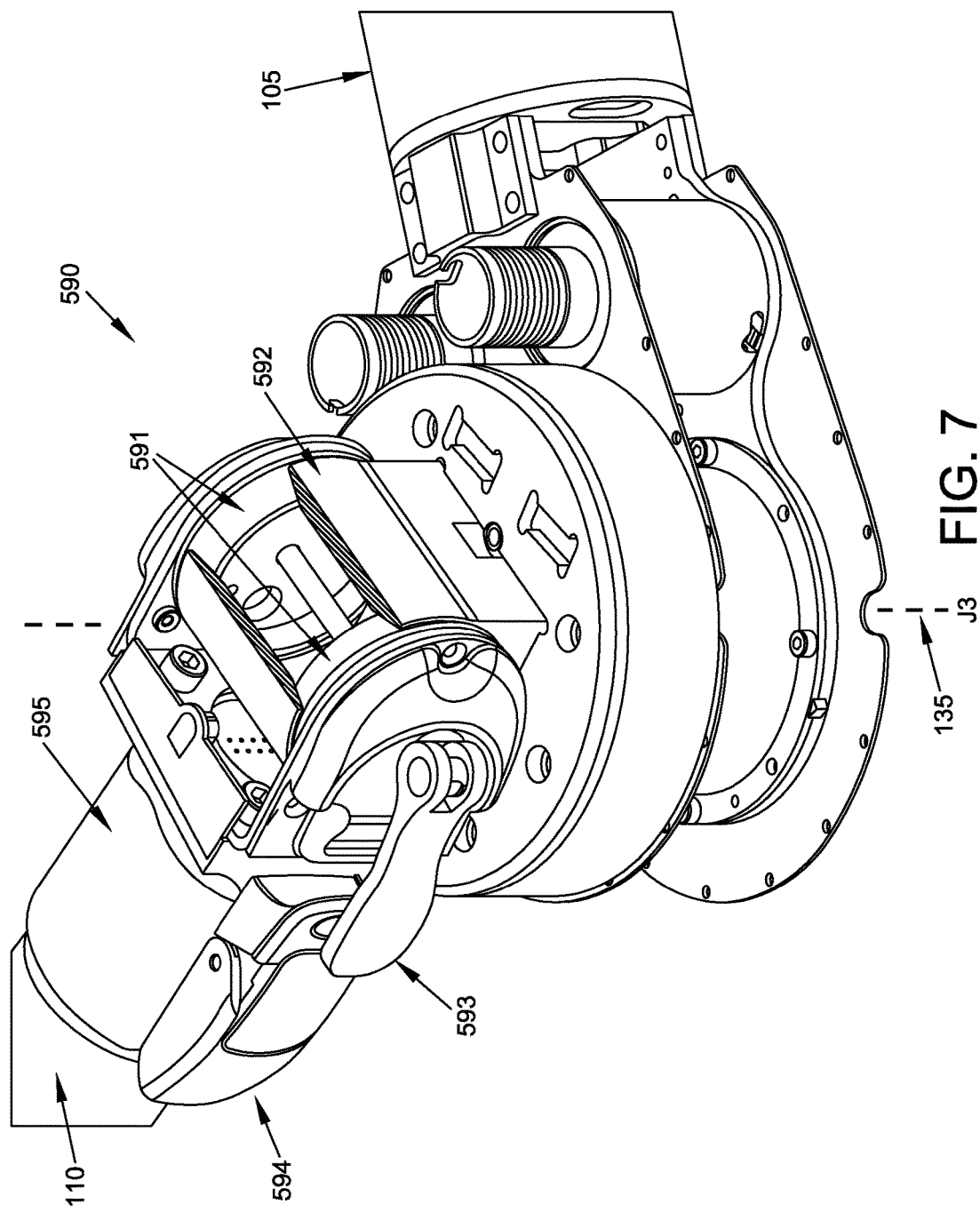

Beyond the output pulley 580 of joint J3, there is generally an outer link 110 (FIGS. 1, 6 and 7), connected to the output pulley 580 (FIGS. 6 and 7) of joint J3 by a mechanism 590 that allows the position of outer link 110 to be adjusted relative to the output pulley 580 of joint J3. Implementing this mechanism 590 (not fully shown in FIG. 6, but shown in FIG. 7), which in a preferred embodiment allows the position of outer link 110 to be moved by some number of degrees (in a more preferred embodiment, 172.5 degrees) about joint J3 axis 135 relative to the output pulley 580 of joint J3, facilitates reversing the chirality of the robotic device, the importance and method of which is described herein. In the preferred embodiment, this mechanism 590 is executed by means of clamping two tabs 591 against a central hub 592 (which is shown in FIG. 7 in cutaway) by means of a toggle lock 593 (e.g., like those commonly found on the forks of bicycles). The contacting faces of the tabs 591 and the central hub 592 are tapered as shown in FIG. 7, to both locate the parts in directions transverse to the direction of force application, and to increase the amount of torque that the clamped parts can resist. It has been found that it is important to ensure that the taper (at the contacting faces of the tabs 591 and the central hub 592) is a non-locking type, so that the system does not jam. This mechanism 590 allows outer link 110 to be flipped across a plane coincident to the axis 135 of joint J3, rather than rotated around the axis 135 of joint J3. While this initially seems like a minor distinction, when implemented with certain types of endpoint attachments, utilizing a mechanism that flips rather than rotates can significantly reduce the time required to reverse the chirality of the robotic device. There are also other components of the sort well known in the art of robotic arms that are not shown here which are used to ensure that the mechanism 590 reaches its desired position, and that the mechanism's position does not shift during operation. By way of example but not limitation, these components may include limit switches, magnets, latches, etc. of the sort well known to a person skilled in the art of robotic arms. There is also a separate mechanism that allows the outer link 110 to be removed from mechanism 590, which facilitates switching between different types of endpoint attachments. In the preferred construction shown in FIG. 7, this is implemented through a latch 594, which firmly clamps outer link 110 inside a tubular member 595 which is firmly attached to tabs 591. This latch 594 is engaged when the robotic device is in use, but may be released to allow the outer link 110 to be removed.

Figure 11:
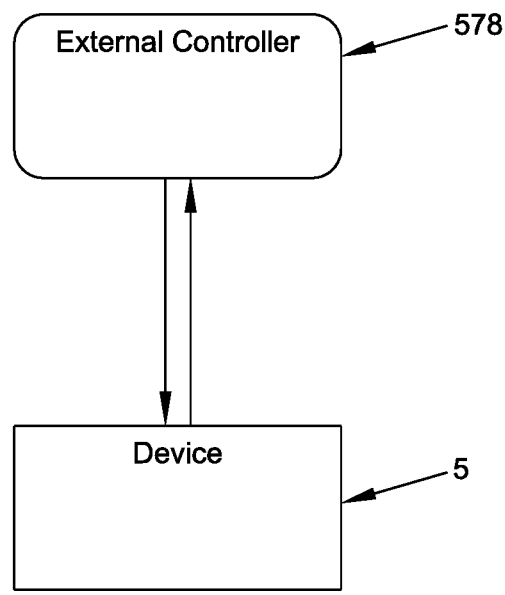
FIG. 11 is a schematic view showing how the robotic device may communicate with an external controller.

Robotic device 5 also comprises an onboard controller and/or an external controller (of the sort which will be apparent to those skilled in the art in view of the present disclosure) for controlling operation of robotic device 5. By way of example but not limitation, FIG. 11 shows how an external controller 578 may be used to control operation of robotic device 5 and/or to receive feedback from robotic device 5 (where robotic device 5 may or not also have an onboard controller).

There may also be other components that are included in the robotic device which are well known in the art of robotic devices but are not shown or delineated here for the purposes of preserving clarity of the inventive subject matter, including but not limited to: electrical systems to actuate the motors (e.g., motors 500 and 565) of the robotic device; other computer or other control hardware for controlling operation of the robotic device; additional support structures for the robotic device (e.g., a mounting platform); covers and other safety or aesthetic components of the robotic device; and structures, interfaces and/or other devices for the patient (e.g., devices to position the patient relative to the robotic device, a video screen for the patient to view while interacting with the robotic device, a patient support such as, but not limited to, a wheelchair for the patient to sit on while using the robotic device, etc.).

Some specific innovative aspects of the present invention will hereinafter be discussed in further detail.

Non-Exoskeletal Device

As discussed above, the robotic device 5 is a non-exoskeletal rehabilitation device. Exoskeletal rehabilitation devices are generally understood as those having some or all of the following characteristics:

joint axes that pierce/are coaxial to the patient's limb joint axes, typically with each patient joint matched to at least one device joint; and device components that capture each of the patient's limbs that are being rehabilitated, typically firmly constraining each limb segment to a member of the device.

In FIG. 1, a simplified representation of the joint axes of a patient's shoulder are shown: the abduction and adduction axis 600, the flexion and extension axis 605, and the internal and external rotation axis 610. Also shown in FIG. 1 is the axis 615 of the patient's elbow joint. As FIG. 1 shows, the joint axes J1, J2 and J3 of robotic device 5 are, by design, non-coaxial with the patient's joint axes 600, 605, 610 and 615. Furthermore, in the preferred embodiment, the patient's limb 120 is only connected to, or captured by, the robotic device 5 at the coupling element 115. In other embodiments of the present invention, there may be multiple coupling points between the patient and the robotic device, which may partially or completely enclose the patient's limb; however, the majority of the structure of the robotic device of the present invention is not capturing the patient's limb.

Because these two conditions are met (i.e., the joint axes J1, J2 and J3 of the robotic device are not intended to be coaxial with the patient's joint axes 600, 605, 610 and 615, and because the patient's limb is not enclosed by the major components of the robotic device 5), the robotic device of the present invention is not an exoskeletal rehabilitation device. While there are many non-exoskeletal rehabilitation devices currently in existence, the non-exoskeletal design of the present device is a critical characteristic distinguishing it from the prior art, since the device incorporates many of the beneficial characteristics of exoskeletal devices while avoiding the cost and complexity that are innate to exoskeletal designs.

Kinematic Relationship of Robotic Device and Patient

Figure 2:
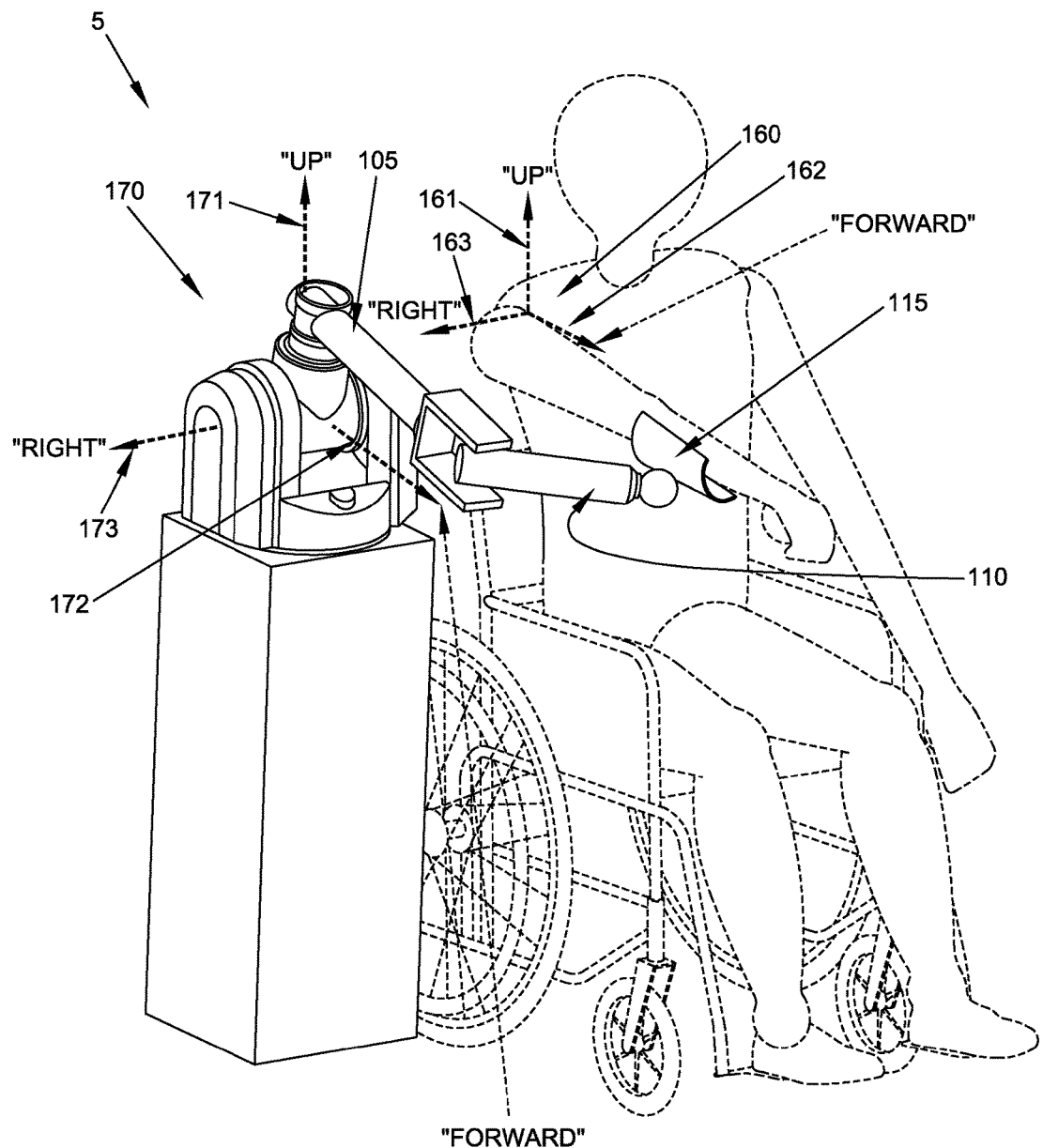
Figure 3:
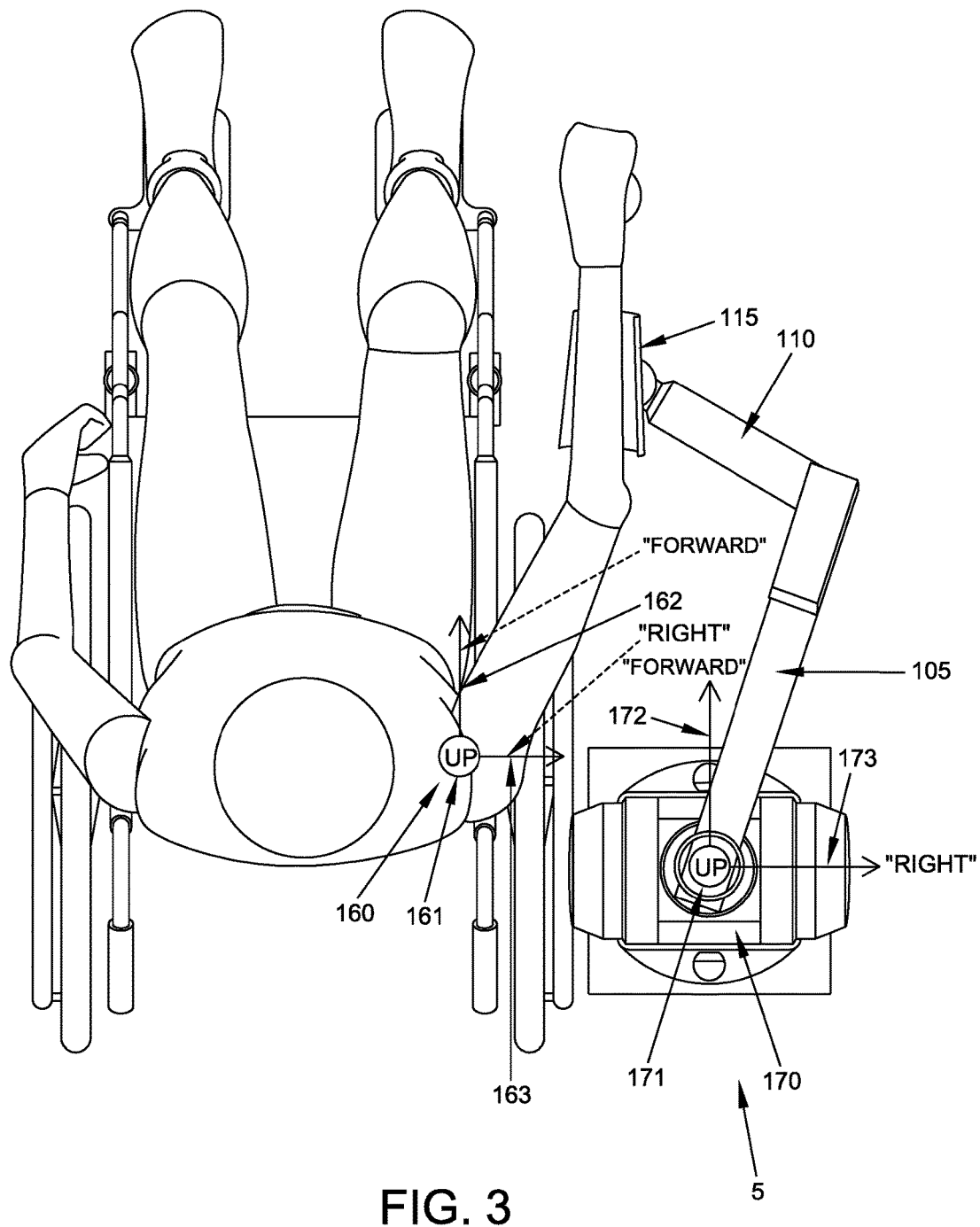
FIGS. 3 and 4 are schematic top views showing the robotic device of FIGS. 1 and 2.

Additionally, FIGS. 2 and 3 show a coordinate reference frame 160 for the patient (consisting of an up axis 161, a forward axis 162 and a right axis 163), as well as a coordinate reference frame 170 for the robotic device 5 (consisting of an up axis 171, a forward axis 172 and a right axis 173). The locations and orientations of these reference frames 160, 170 defines a kinematic relationship between (i) the robotic device 5 and its links 105, 110, and (ii) the patient and their limb: the robotic device 5 is designed such that its motions mimic those of the patient, in that a given motion of the patient's endpoint in the reference frame 160 of the patient will be matched by a generally similar motion of the device's endpoint in the reference frame 170 of robotic device 5. This relationship is important to the definition of many of the innovative aspects of the device, as shown below.

Before further explaining this concept, it is helpful to provide some terminology. The "patient reference frame" (or PRF) 160 and the "device reference frame" (or DRF) 170, as used here, are located and oriented by constant physical characteristics of the patient and device. As shown in FIGS. 2 and 3, the origin of the PRF 160 is defined at the base of the patient's limb which is coupled to the robotic device, and is considered fixed in space. The "up" vector 161, which is treated as a "Z" vector in a right-handed coordinate system, is defined to point from this origin in the commonly accepted "up" direction (against the direction of gravity). The "forward" vector 162 is likewise defined in the commonly accepted "forward" direction, in front of the patient. More precisely, it is treated as a "Y" vector in a right-handed coordinate system, and is defined as the component of the vector pointing from the origin to the center of the limb's workspace which is perpendicular to the "up" vector. Finally, the "right" vector 163 points to the right of the patient. Rigorously defined, it is treated as an "X" vector in a right-handed coordinate system, and is consequently defined by the other two vectors. Thus, a reference frame 160 is defined for the patient which is located and oriented entirely by constant physical characteristics and features. While this coordinate frame definition has been executed in FIGS. 2 and 3 for a patient's arm, this definition method can easily be extended to other limbs, such as a leg.

A similar reference frame is defined for the robotic device. The origin is placed at the centroid of the base of the robotic device 5, which must also be fixed in space. The "forward" vector 172 is defined as the component of the vector pointing from the origin to the geometric centroid of the device's workspace. The "up" vector 171 and the "right" vector 173 may be defined in arbitrary directions, so long as they meet the following conditions:

1) They are mutually perpendicular;
2) They are both perpendicular to the "forward" vector 172;
3) They meet the definition of a right-handed coordinate system wherein the "up" vector 171 is treated as a Z vector, the "right" vector 173 is treated as an X vector, and the "forward" vector 172 is treated as a Y vector; and
4) Preferably, but not necessarily, the "up" vector 171 is oriented as closely as possible to the commonly accepted "up" direction (against the direction of gravity).

In some cases, such as with the REOGO® arm rehabilitation system of Motorika Medical Ltd. of Mount Laurel, N.J., USA, the aforementioned condition "4)" cannot be satisfied because the device's "forward" vector already points in the generally accepted "up" direction; consequently, the "up" vector may be defined arbitrarily subject to the three previous conditions. This case is further detailed below.

When existing rehabilitation devices are separated into exoskeletal and non-exoskeletal devices as per the description above, a further distinction between these two groups becomes apparent based on this definition of reference frames. In exoskeletal devices, the robotic device and the patient operate with their reference frames (as defined above) oriented generally similarly: "up", "right" and "forward" correspond to generally the same directions for both the patient and the robotic device, with the misalignment between any pair of directions in the PRF and DRF respectively preferably no greater than 60 degrees (i.e. the "forward" direction in the DRF will deviate no more than 60 degrees from the "forward" direction in the PRF), and preferably no greater than 45 degrees. Meanwhile, to date, a non-exoskeletal device in which the robotic device and the patient reference frames are generally oriented similarly in this way has not been created. Devices available today are oriented relative to the patient in a number of different ways, including the following:

The DRF may be rotated 180° around the "up" axis relative to the PRF so that the device "faces" towards the patient, or 90°, so that the device "faces" perpendicular to the patient: for example, in the INMOTION ARM™ system of Interactive Motion Technologies of Watertown, Mass., USA; the HapticMaster haptic system of Moog Incorporated of East Aurora, N.Y., USA; the DEXTREME™ arm of BioXtreme of Rehovot, Israel; or the KINARM END-POINT ROBOT™ of BKIN Technologies of Kingston, Ontario, Canada. In the case of the DEXTREME™ arm, for instance, the device is designed to be used while situated in front of the patient. Its workspace, which is generally shaped like an acute segment of a right cylinder radiating from the device's base, likewise faces towards the patient. When a coordinate reference frame is generated for the device's workspace as outlined above, the "forward" direction—which points from the centroid of the base of the device to the centroid of the device's workspace—will be found to point towards the patient. Consequently, the device's reference frame is not oriented similarly to that of the patient.

Alternatively, the DRF may be rotated 90° about the "right" axis relative to the PRF such that the device's "forward" axis is parallel to the patient's "up" axis; or other combinations. One example is the REOGO® arm rehabilitation system of Motorika Medical Ltd of Mount Laurel, N.J., USA, where the device's base sits underneath the patient's arm undergoing rehabilitation, and its primary link extends up to the patient's arm. Its workspace is generally conical, with the tip of the cone located at the centroid of the base of the device. When a coordinate reference frame is generated for the device as outlined above, the "forward" vector of the device will be found to have the same direction as the "up" vector in the patient's reference frame. Consequently, the device's reference frame is not oriented similarly to that of the patient.

Finally, devices like the ArmAssist device of TECNALIA® of Donostia-San Sebastián, Spain may not have a definable DRF. The ArmAssist device is a small mobile platform which is designed to sit on a tabletop in front of the patient. The patient's arm is attached to the device, which then moves around the tabletop to provide rehabilitative therapy. Since the ArmAssist device is fully mobile, a fixed origin cannot be defined for it as per the method outlined above, and it is not relevant to this discussion.

The robotic device of the present invention is the first non-exoskeletal device which is designed to operate with its reference frame 170 oriented generally similarly to the reference frame 160 of the patient. This innovation allows the robotic device to leverage advantages that are otherwise limited to exoskeletal devices, including:

Reduced interference with the patient's line of sight or body, since the robotic device does not need to sit in front of/to the side of the patient.

More optimal position-torque relationships between patient and device, since the moment arms between the device and patient endpoints and their joints are directly proportional to one another, rather than inversely proportional to one another as in other devices. For example, when the device's links are extended, the patient's limb undergoing rehabilitation will be generally extended as well. While the device is not able to exert as much force at its endpoint as it can when the endpoint is closer to the device's joints, the patient's force output capacity will be likewise reduced. Similarly, when the patient's limb is contracted and the force output is maximized, the device's endpoint will be closer to its joints, and its endpoint output force capacity will be maximized.

Better workspace overlap between the patient and the device, since the device's links extend from its base in the same general direction that the patient's limb extends from the body.

Figure 4:
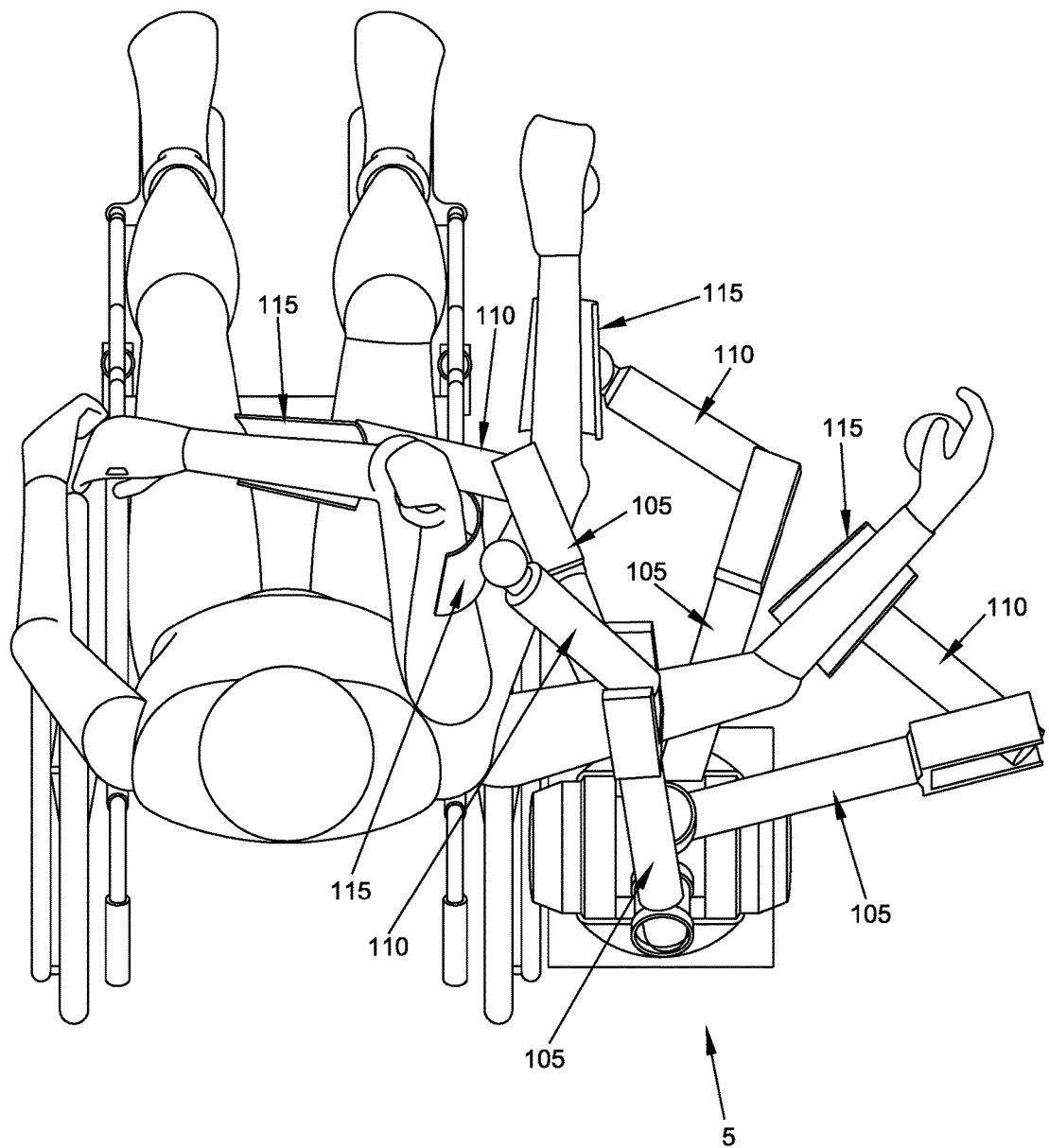

Like an exoskeletal device, the robotic device 5 generally mimics the movements of the patient's limb, in that the endpoint of the device tracks the patient's limb, and a given motion in the reference frame 160 of the patient produces motion in a generally similar direction in the device's reference frame 170. For example, if the patient moves their limb to the right in the patient's reference frame 160, the device's links will generally move to the right in the device's reference frame 170, as shown in FIG. 4. However, unlike an exoskeletal device, the individual links and joints of the robotic device do not necessarily mimic the motions of individual parts or joints of the patient's limb, even though the endpoint of the robotic device does track the patient's endpoint. As shown in FIG. 4, in the preferred embodiment, motions in front of the patient cause both the patient's limb and the links 105, 110 of robotic device 5 to extend; by contrast, in FIG. 4, motions to the far right of the patient cause the patient's limb to straighten while the links 105, 110 of the robotic device 5 bend. By operating without this constraint (i.e., that the individual links and joints of the robotic device do not necessarily mimic the motions of the individual parts or joints of the patient's limb), the robotic device 5 avoids many of the weaknesses inherent in exoskeletal devices, particularly the bulk, complexity, cost and setup time associated with directly replicating the kinematics of a limb.

Because of the need for this distinction between the robotic device of the present invention and exoskeletal devices (i.e., that a relationship cannot easily be defined between the patient's limb and the links of the robotic device), it is necessary to define the relationship between the robotic device and the patient as a function of the bases, endpoints and orientations of the robotic device and the patient. By defining device and patient reference frames in this manner, the previous statement that "the robotic device 5 is designed such that its motions mimic those of the patient, in that a given motion of the patient's endpoint in the reference frame 160 of the patient will be matched by a generally similar motion of the device's endpoint in the reference frame 170 of robotic device 5" is satisfied only when the robotic device 5 is oriented relative to the patient as described herein.

A series of simple logical tests have been developed to aid in determining whether a device meets the criteria outlined above. For these tests, the device is assumed to be in its typical operating position and configuration relative to the patient, and a PRF is defined for the patient's limb undergoing rehabilitation as described above.

1) Is the device an exoskeletal rehabilitation device, as defined previously?
   a. YES: Device does not meet criteria—criteria are only applicable to non-exoskeletal devices.
   b. NO: Continue.
2) Can an origin that is fixed relative to the world reference frame and located at the centroid of the base of the device be defined?
   a. YES: Continue.
   b. NO: Device does not meet criteria—criteria are not applicable to mobile devices.
3) Consider the device's workspace, and find the geometric centroid of that workspace. Can a "forward" or Y vector be defined between the geometric centroid of the device's workspace and the device's origin?
   a. YES: Continue.
   b. NO: Device does not meet criteria.
4) Can the "up"/Z vector and the "right"/X vector be defined as outlined above relative to the forward vector?
   a. YES: Continue.
   b. NO: Device does not meet criteria—it is likely designed for a significantly different rehabilitation paradigm than the device disclosed here.
5) Are the workspaces of the device and patient oriented generally similarly, in that the "right"/X, "forward"/Y and "up"/Z vectors of both coordinate reference frames have generally the same direction, with a deviation of less than a selected number of degrees between any pair of vectors? (In the preferred embodiment, this is preferably less than 60 degrees, and more preferably less than 45 degrees.)
   a. YES: Continue.
   b. NO: The device does not meet the criteria outlined—it is positioned differently relative to the patient than the device outlined here.
6) Are motions of the patient's endpoint mimicked or tracked by similar motions of the device's endpoint?
   a. YES: The device meets the criteria outlined.
   b. NO: The device does not meet the criteria outlined.

To date, no device with more than 2 degrees of freedom, other than the system described here, has been found that successfully passes this series of tests.

Stated another way, generally similar orientation between the patient and the device can be examined by identifying a "forward" direction for both the user and the device. In the patient's case, the "forward" direction can be defined as the general direction from the base of the patient's arm undergoing rehabilitation, along the patient's limb, towards the patient's endpoint when it is at the position most commonly accessed during use of the device. In the device's case, the "forward" direction can be defined as the general direction from the base of the device, along the device's links, towards the device's endpoint when it is at the position most commonly accessed during use of the device. If the "forward" direction of the device and "forward" direction of the patient are generally parallel (e.g., preferably with less than 60 degrees of deviation, and more preferably with less than 45 degrees of deviation), then the device and the user can be said to be generally similarly oriented.

General Location of System

One preferred embodiment of the present invention is shown in FIGS. 3 and 4, where the robotic device 5 is positioned to the side of, and slightly behind, the patient (in this case, with the axis 125 of the joint J1 behind, or coincident to, the patient's coronal plane). In this embodiment, the reference frame 170 of the robotic device 5 and the reference frame 160 of the patient are oriented generally similarly, as described above. The robotic device 5 is kept out of the patient's workspace and line of sight, making it both physically and visually unobtrusive. The workspaces of the robotic device and patient overlap to a high degree. The range of motion allowed by this positioning is still quite large, as shown in FIG. 4, and approaches or exceeds that allowed by high-DOF exoskeletal systems.

It should be noted that while this arrangement (i.e., with the robotic device 5 positioned to the side of, and slightly behind, the patient) has been found to be preferable for certain rehabilitative therapies, there are other embodiments in which the robotic device 5 is positioned differently relative to the patient which may be better suited to other applications, such as use as a haptic input/control device, or other rehabilitative activities. For example, in the case of advanced-stage arm rehabilitation, in situations where the patient is reaching up and away from the device, it may prove optimal to place the robotic device slightly in front of the patient.

Link Stacking Order

Figure 5:
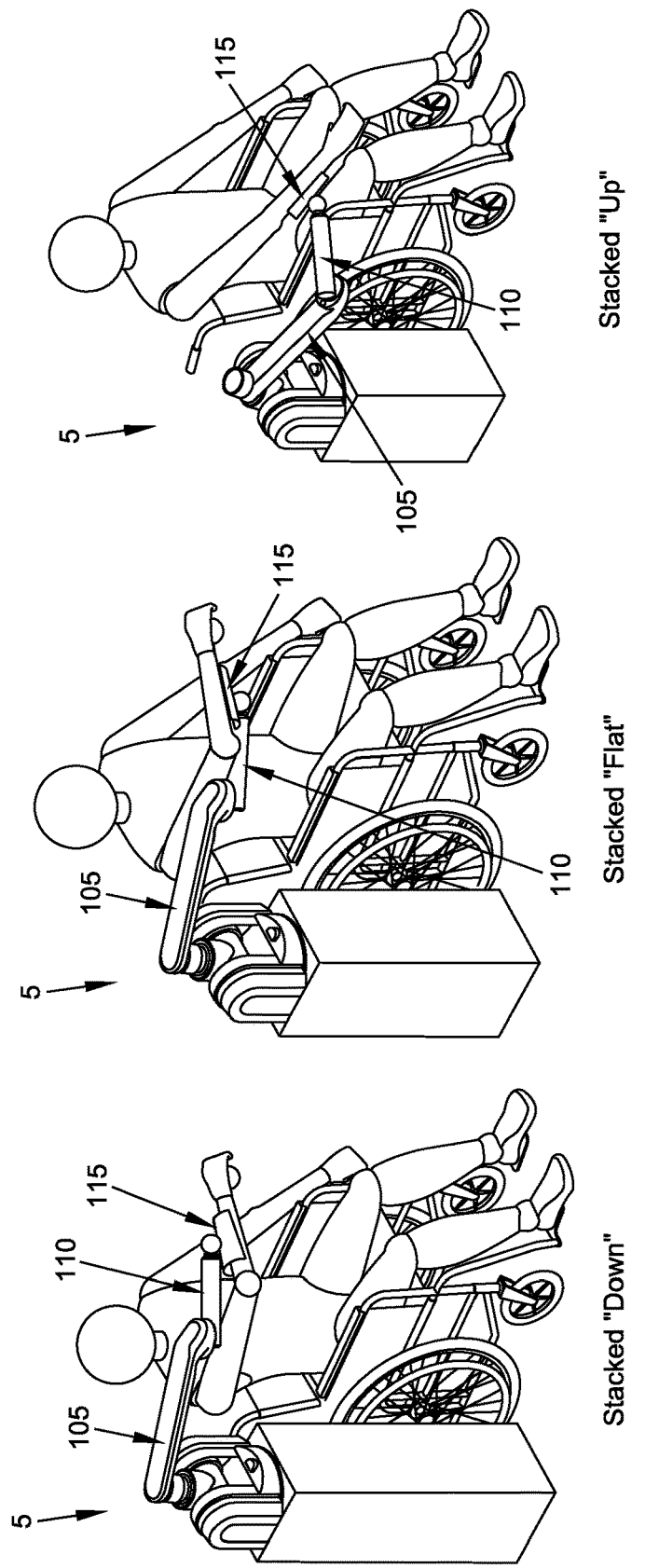
FIGS. 5A, 5B and 5C are schematic front perspective views showing how the robotic device of FIGS. 1 and 2 may use a "stacked down", "stacked flat" or "stacked up" construction.

Looking next at FIGS. 5A, 5B and 5C, several novel implementations of the system are shown wherein the device's links 105, 110 are ordered in different directions to facilitate different activities. By way of example but not limitation, FIG. 5A shows a configuration referred to as the "stacked-down" configuration, in which the outer link 110 of the robotic device 5 is attached to the underside of the inner link 105 of the robotic device 5, allowing the device to reach from above the patient, downwards, to their limb (attached via coupling element 115). FIG. 5C shows a configuration referred to as the "stacked-up" configuration, in which the outer link 110 of the robotic device 5 is attached to the top side of inner link 105 of the robotic device 5, allowing the device to reach from below the patient, upwards, to their limb (attached via coupling element 115). Both implementations may prove optimal in different situations. The "stacked-down" variant is less likely to interfere with the patient's arm during rehabilitation activity because of its position above the patient's workspace, and may prove more useful for high-functioning rehabilitation patients who require expanded workspace. Conversely, the "stacked-up" variant is better able to support a patient's arm, and is less likely to interfere with the patient's visual workspace; it is better suited for low-functioning patients. FIG. 5B shows a configuration referred to as the "stacked flat" configuration, in which the outer link 110 of the robotic device 5 is attached to the bottom side of inner link 105 of the robotic device 5, and coupling element 115 is attached to the top side of outer link 110, allowing the device to reach the patient so that the forearm of the patient is approximately flat with inner link 105.

Cabled Differential, with Alternative Configurations

FIG. 6 illustrates an important aspect of the present invention, i.e., the use of a cabled differential (see, for example, U.S. Pat. No. 4,903,536) in a rehabilitation device. The preferred embodiment of the robotic device 5 comprises three revolute joints J1, J2 and J3, implemented in a pitch-yaw-yaw configuration (FIG. 1), with the first two joints (i.e., J1 and J2) linked in a cabled differential as shown in FIG. 6. As shown in FIG. 6, the use of a cabled differential allows a motor that would normally be mounted on a higher-level kinematic frame to be moved down to a lower-level frame. For example, in the preferred embodiment shown in FIG. 6, the motors 500 that cause rotation about joint J1 and joint J2 are moved from the aforementioned joint J1 kinematic frame (which rotates about the axis 125 of joint J1 down to the aforementioned ground kinematic frame (the ground frame; collocated with base 100 in FIG. 1). This significantly reduces the inertia that the motors 500 are required to move, which improves the performance of the robotic device and reduces its cost by permitting smaller motors 500 to be used. Although this is implemented in the preferred embodiment at the base of the robotic device, the principle behind this design is valid anywhere along a device's kinematic chain. This is a particularly important innovation in the context of a rehabilitation device because of its ability to reduce the device's cost, which must be kept low to ensure the commercial success of the device. This configuration also allows the exclusive use of rotary joints (instead of prismatic joints), which greatly simplifies the design of the device. Lower inertia also improves the safety of the device by lowering the momentum of the device. Finally, this innovation also maximizes usability by allowing the visual bulk of the device to be shifted away from the patient's line of sight towards the base of the device. While this concept is executed as part of a rehabilitation device with three degrees of freedom in the preferred embodiment, it is clearly applicable to other rehabilitation devices with as few as two degrees of freedom.

Furthermore, in the preferred embodiment shown in FIGS. 1 and 6, the implementation of a cabled differential with the input and output axes (i.e., the axes of input pulleys 505 and output pulley 540) both perpendicular to the distal link axis (i.e., the axis along inner link 105) provides the benefits of a cable differential while allowing the unique pitch-yaw kinematic arrangement that makes this device so well suited to rehabilitation use. Previous implementations of cabled differentials have either been arranged in a pitch-roll configuration such as in the Barrett WAM product of Barrett Technology, Inc. of Newton, Mass. as shown at 700 in FIG. 8C, or in a roll-pitch configuration such as in the Barrett WAM wrist product as shown at 720 in FIG. 8B. In both of these implementations (i.e., the pitch-roll configuration 700 of FIG. 8C and the roll-pitch configuration 720 of FIG. 8B), either the distal link (i.e., the link beyond the differential in the kinematic chain) or the proximal link (i.e., the link before the differential in the kinematic chain) is permanently coaxial with one of the two differential rotational axes. In the case of the pitch-roll configuration 700 of FIG. 8C, the outer link 710 is always coaxial to the differential output axis 705; in the roll-pitch configuration 720 of FIG. 8B, the inner link 725 is always coaxial to the differential input axis 730.

To date, however, the cabled differential has not been used in a configuration where neither of the differential axes is coaxial to one of the links. This configuration has been successfully implemented in the preferred embodiment of the present invention, as seen in both FIG. 6 (see the pitch-yaw configuration of joints J1 and J2 relative to the inner link of the device 105) and in FIG. 8A, where the novel pitch-yaw configuration 740 is shown. This new implementation of the cable differential enables innovative kinematic configurations like that used in the present invention.

Bimanual Multi-Dimensional Rehabilitation Exercises and Device Design

Figure 9:
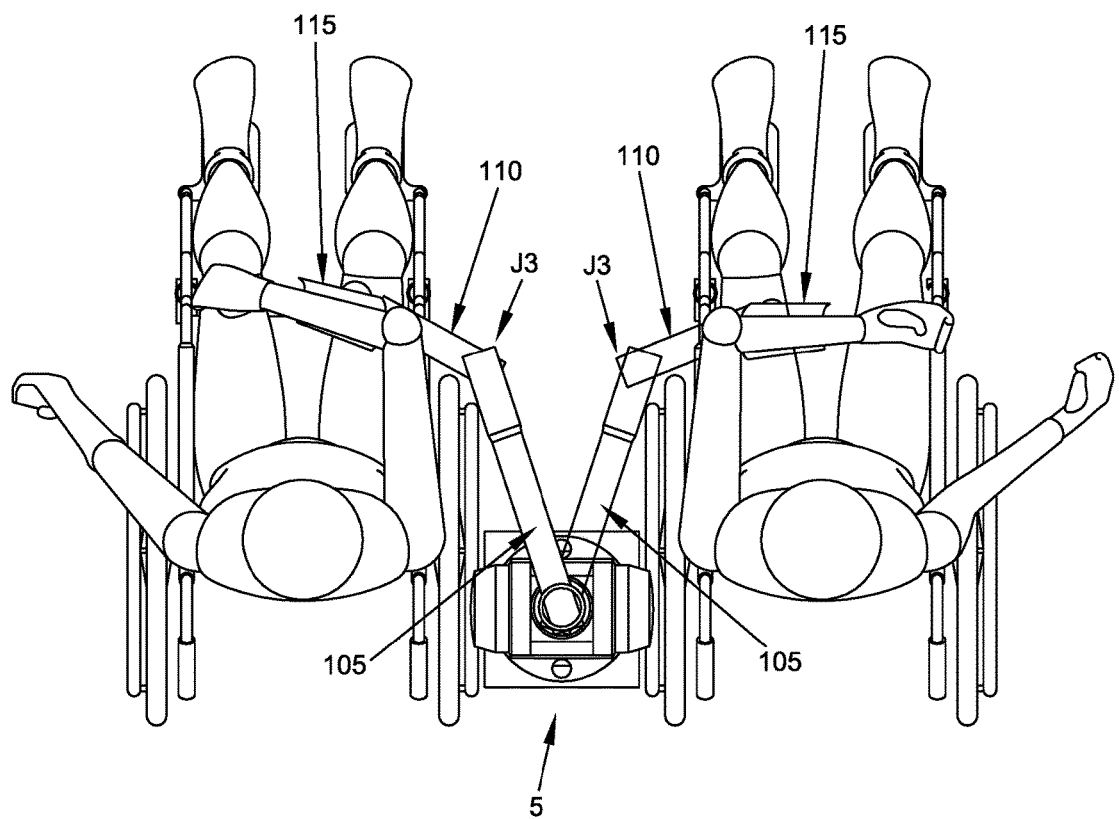
FIG. 9 is a schematic top view showing how the robotic device of the present invention may be switched from right-handed use to left-handed use.

FIG. 9 shows how the preferred embodiment of the robotic device 5 is optimal for the purposes of switching from right-handed to left-handed use. The robotic device 5 is essentially symmetric across a plane parallel to the patient's midsagittal plane and coincident with the axis 130 of joint J2. By simply ensuring that the range of joint J2 is symmetric about the previously described plane, and enabling the outer link 110 to be reversed about the axis 135 of joint J3 such that its range of motion is symmetric about the previously described plane in either position, the device's chirality can easily be reversed, enabling it to be used on either the right side or left side of the patient's body as seen in FIG. 9.

Figure 10:
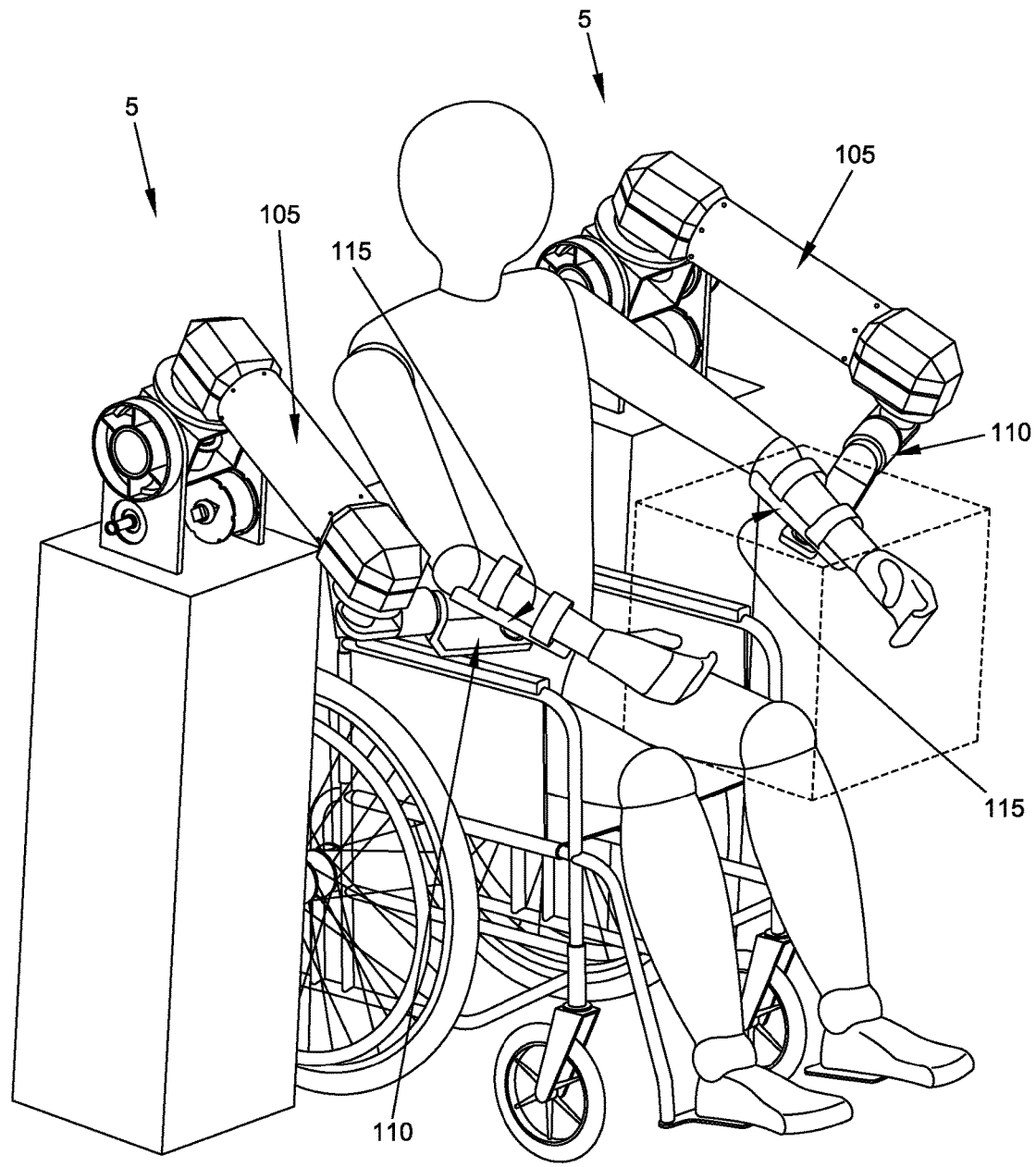
FIG. 10 is a schematic view showing two robotic devices being used for bimanual rehabilitation.
Figure 12:
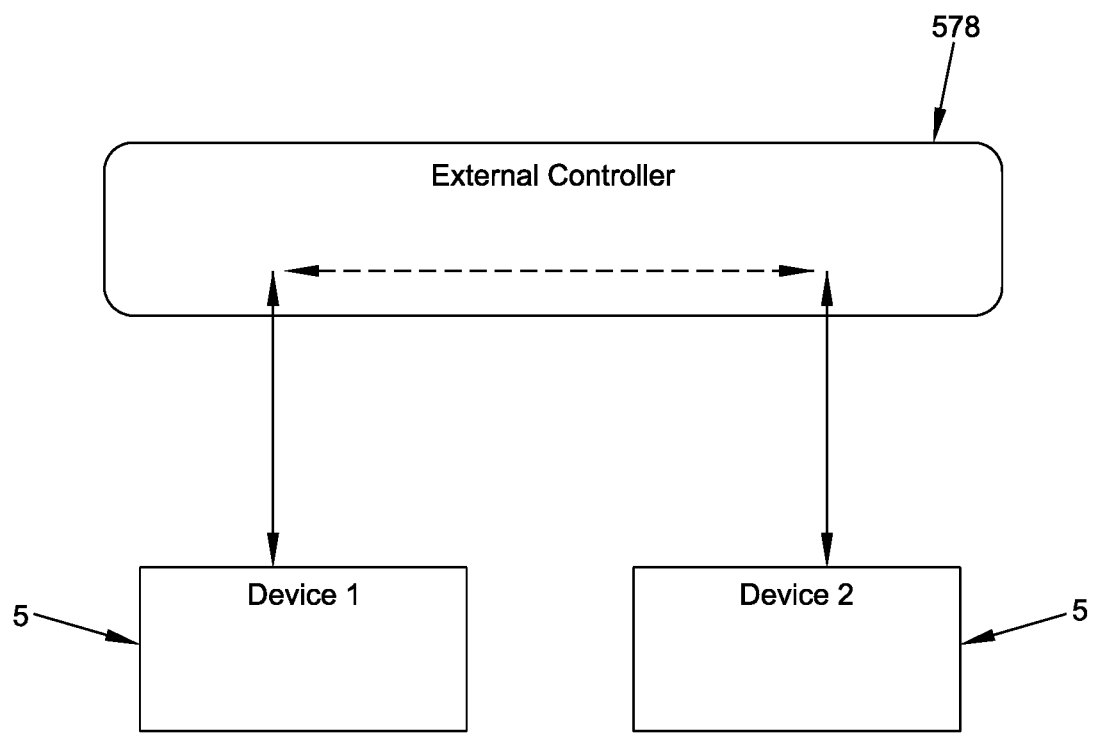
FIG. 12 shows how a pair of robotic devices may communicate with an external controller, which in turn facilitates communication between the devices.

Finally, FIG. 10 illustrates how the innate symmetry and reversible chirality of robotic device 5 combine with its unique working position/orientation and small size to allow two units of the robotic device to be used simultaneously for three-dimensional bimanual rehabilitation. In bimanual rehabilitation, the afflicted limb is paired with a non-afflicted limb in rehabilitation activities, including cooperative tasks, such as using both limbs to lift an object; and instructive tasks, where the healthy limb "drives" the afflicted limb. The value of bimanual rehabilitation (particularly in the context of rehabilitation from a neuromuscular injury such as a stroke, which can make execution of neurologically complex tasks like coordinated movement between limbs on opposite sides of the body exceedingly difficult) was theorized as early as 1951, and has gained significant traction over the past 20 years. See "Bimanual Training After Stroke: Are Two Hands Better Than One?" Rose, Dorian K. and Winstein, Carolee J. Topics in Stroke Rehabilitation; 2004 Fall; 11(4): 20-30. Robotic rehabilitation devices are extremely well suited to this type of therapy, due to their ability to precisely control the motion of the patient's limbs and coordinate with other rehabilitation devices. In an exemplary implementation shown in FIG. 10, a first robotic device 5 is connected to the patient's afflicted right arm, while a second robotic device 5 is connected to a more functional left arm. The robotic devices are linked to each other through some type of common controller (e.g., as seen in FIG. 12, an external controller 578 that communicates with the onboard controllers of both robotic devices 5, while facilitating communication between the two devices), which coordinates the rehabilitation therapy. While this example is demonstrated using images of the preferred embodiment of the robotic device, it may be understood that the essential concept of bimanual rehabilitation may be implemented with any variety of devices, even if those devices are dissimilar. However, there are significant advantages to using two similar robotic devices 5 for bimanual rehabilitation, which are disclosed below, and which lead to a novel method for bimanual rehabilitation.

The robotic device 5 described here is the first non-planar rehabilitation device to be purpose-designed for this type of dual-device, simultaneous use in a three-dimensional bimanual system. As described earlier, the robotic device's innate symmetry allows its chirality to be easily reversed, allowing the same robotic device design to be used for rehabilitation of both right and left limbs. Furthermore, the device's small footprint facilitates simultaneous use of two systems, as shown in FIG. 10. While other devices, such as the ARMEO™ Power system of Hocoma AG of Volketswil, Switzerland, are similarly reversible, the size of these systems and their position relative to the patient precludes their use in a bimanual rehabilitation system, since the bases of the two systems would interfere. There are also some devices that have been deliberately designed for bimanual rehabilitation, such as the EXOSKELETON™ and END-POINT™ robots of BKIN Technologies of Kingston, Ontario, Canada. However, as mentioned above, these devices are deliberately limited to planar (two-dimensional) rehabilitative therapies, significantly impacting their utility for patients.

There exists one known example of a system that is nominally capable of performing limited 3-dimensional bimanual rehabilitation therapies with only unimanual actuation, i.e., the $3^{rd}$-generation Minor-Image Motion Enabler (MIME) rehabilitation robot, developed as a collaborative project between the Department of Veterans Affairs and Stanford University in 1999. See "Development of robots for rehabilitation therapy: The Palo Alto VA/Stanford experience." Burgar et. al. *Journal of Rehabilitation Research and Development. Vol.* 37 No. 6, November/December 2000, pp. 663-673. The $3^{rd}$-generation MIME robot consists of a PUMA-560 industrial robot affixed to the patient's afflicted limb, and a passive six-axis MicroScribe digitizer affixed to a splint, which is in turn coupled to the patient's healthy limb. In the system's bimanual mode, motions of the healthy limb are detected by the digitizer and passed to the robotic arm, which moves the afflicted limb such that its motions mirror those of the healthy limb. While this system can execute a limited set of bimanual rehabilitation therapies, it is fundamentally limited by the unidirectional flow of information within the system: information can be passed from the healthy limb to the afflicted limb, but not back from the afflicted limb to the healthy limb, since the digitizer is passive and does not have motors or other mechanisms with which to exert forces on the patient's healthy limb.

In the implementation described herein, the use of two similar, active robotic devices 5—in the preferred implementation, with similar kinematics, joint ranges, force output limits and static and dynamic performance characteristics—enables bidirectional information flow (i.e., bidirectional informational flow wherein both devices send, receive and respond to information from the other device), creating a bimanual rehabilitation system that is capable of monitoring the position of both the afflicted and healthy limbs, moving the patient's afflicted limb in three dimensions and potentially controlling its orientation simultaneously, and optionally providing simultaneous force feedback, support or other force inputs to the healthy limb. For example, the robotic device connected to the patient's healthy limb can be used to "drive" the robotic device connected to the patient's afflicted limb, while simultaneously supporting the healthy limb to prevent fatigue, and providing force feedback to the healthy limb as required by the therapy. In this respect it has been found that the cable drives used in the preferred implementation of the present invention are particularly well suited to this type of use, because of the high mechanical bandwidth of cable drive transmissions; however, alternative embodiments could be implemented using alternative mechanical drive systems. Regardless of specific implementation, this bidirectional information flow—when executed between two similar devices with the facilitating characteristics described here—allows the device to be used for a far wider range of three-dimensional bimanual rehabilitative therapies than prior art systems and enables the method disclosed herein.

Additional Applications for the Present Invention

In the preceding description, the present invention is discussed in the context of its application for a rehabilitation device. However, it will be appreciated that the present invention may be utilized in other applications, such as applications requiring high-fidelity force feedback. By way of example but not limitation, these applications may include use as an input/haptic feedback device for electronic games, as a controller for other mechanical devices, such as industrial robotic arms or construction machines, or as a device for sensing position, i.e., as a digitizer or coordinate measuring device.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A robotic device for operation in association with a body of a user, wherein the body of the user comprises a torso and an appendage, wherein the appendage of the user has an endpoint, an appendage segment, a first joint movably connecting the endpoint to the appendage segment, and a second joint movably connecting the appendage segment to the torso of the user, the robotic device comprising:
   a base having a fixed configuration, the base being configured for disposition behind, and to the side of, the torso of the user;
   a first segment movably mounted to the base so as to rotate around a first axis, whereby to provide a first degree of freedom;
   a second segment movably mounted to the first segment so as to rotate around a second axis, whereby to provide a second degree of freedom;
   a third segment mounted to the second segment; and
   a fourth segment movably mounted to the third segment so as to rotate around a third axis, whereby to provide a third degree of freedom, the fourth segment having an endpoint, the endpoint of the fourth segment being configured for attachment to the endpoint of the appendage of the user and the fourth segment being configured to be free of attachment to the appendage segment of the user;
   wherein the first axis is disposed substantially horizontal, the second axis is disposed orthogonal to the first axis, and the third axis is disposed parallel to the second axis; and
   wherein, when the endpoint of the fourth segment is attached to the endpoint of the appendage of the user, the first segment, the second segment, the third segment and the fourth segment move during movement of the appendage of the user, and none of the first axis, the second axis, and the third axis are disposed coaxial with either the first joint or the second joint of the appendage of the user.

2. A robotic device according to claim 1 wherein the first and second degrees of freedom of the robotic device are linked through a cabled differential.

3. A robotic device according to claim 2 wherein the cabled differential comprises an input axis and an output axis, wherein the third segment is coupled to the cabled differential, wherein the third segment extends along an axis, and wherein both the input axis and the output axis of the cabled differential are perpendicular to the axis of the third segment.

4. A robotic device according to claim 1 further comprising motors, wherein the base of the robotic device comprises a ground frame and the robotic device comprises kinematic frames at each degree of freedom, and wherein the motors are located on kinematic frames beyond the ground frame.

5. A robotic device according to claim 1 wherein the robotic device is configured to be symmetric about a plane parallel to the midsagittal plane of a user during use.

6. A robotic device according to claim 1 wherein the third and fourth segments are stacked downwards.

7. A robotic device according to claim 1 wherein the third and fourth segments are stacked upwards.

8. A robotic device according to claim 1 wherein the endpoint of the robotic device is replaceable by another endpoint providing different functionality.

9. A robotic device according to claim 1 wherein the 3 degrees of freedom are arranged in a pitch-yaw-yaw configuration, wherein the first and second segments of the robotic device are linked through a cabled differential, wherein an actuator for the fourth segment is located along the first axis, and wherein the fourth segment of the robotic device is configured to facilitate switching between right-handed use and left-handed use.

10. A robotic device according to claim 1 wherein rotation around the first axis provides pitch, and rotation around the second and third axes provides yaw.

11. A robotic device according to claim 1 wherein the second segment is attached perpendicularly to the first segment.

12. A robotic system comprising:
   a first robotic device for operation in association with a body of a user, wherein the body of the user comprises a torso and two appendages, wherein the first appendage of the user has a first endpoint, a first appendage segment, a first joint movably connecting the first endpoint to the first appendage segment, and a second joint movably connecting the appendage segment to the torso of the user;
   a second robotic device for operation in association with a second appendage of the body of the user, wherein the second appendage of the user has a second endpoint, a second appendage segment, a third joint movably connecting the second endpoint to the second appendage segment, and a fourth joint movably connecting the appendage segment to the torso of the user, the first and second robotic devices each comprising:
      a base having a fixed configuration, the base being configured for disposition behind, and to the side of, the torso of the user;
      a first segment movably mounted to the base so as to rotate around a first axis, whereby to provide a first degree of freedom;
      a second segment movably mounted to the first segment so as to rotate around a second axis, whereby to provide a second degree of freedom;
      a third segment mounted to the second segment; and
      a fourth segment movably mounted to the third segment so as to rotate around a third axis, whereby to provide a third degree of freedom, the fourth segment having an endpoint;
   wherein the endpoint of the fourth segment of the first robotic device is configured for attachment to the first endpoint of the first appendage of the user and the fourth segment of the first robotic device is configured to be free of attachment to the first appendage segment of the user;
   wherein the second endpoint of the fourth segment of the second robotic device is configured for attachment to the second endpoint of the second appendage of the user and the fourth segment of the second robotic device is configured to be free of attachment to the second appendage segment of the user; and wherein the first robotic device and the second robotic device are paired so that the first robotic device and the second robotic device move in conjunction with one another;

wherein the first axis of the first robotic device and the first axis of the second robotic device are disposed substantially horizontal, the second axis of the first robotic device and the second axis of the second robotic device are disposed orthogonal to the first axis of the first robotic device and the first axis of the second robotic device, respectively, and the third axis of the first robotic device and the third axis of the second robotic device are disposed parallel to the second axis of the first robotic device and the second axis of the second robotic device, respectively; and wherein, when the endpoint of the fourth segment of the first robotic device is attached to the first endpoint of the appendage of the user, and when the endpoint of the fourth segment of the second robotic device is attached to the second endpoint of the second appendage of the user, the first segment, the second segment, the third segment and the fourth segment of both the first robotic device and the second robotic device move during movement of the first and second appendages of the user, respectively, and none of the first axis, the second axis, and the third axis of either the first robotic device or the second robotic device are disposed coaxial with either the first joint or the second joint of either the first or second appendages of the user.

13. A method comprising:
providing a robotic system comprising:
a first robotic device for operation in association with a first appendage of a body of a user, wherein the body of the user comprises a torso and two appendages, wherein the first appendage of the user has a first endpoint, a first appendage segment, a first joint movably connecting the first endpoint to the first appendage segment, and a second joint movably connecting the appendage segment to the torso of the user;
a second robotic device for operation in association with a second appendage of the body of the user, wherein the second appendage of the user has a second endpoint, a second appendage segment, a third joint movably connecting the second endpoint to the second appendage segment, and a fourth joint movably connecting the appendage segment to the torso of the user, the first and second robotic devices each comprising:
a base having a fixed configuration, the base being configured for disposition behind, and to the side of, the torso of the user;
a first segment movably mounted to the base so as to rotate around a first axis, whereby to provide a first degree of freedom;
a second segment movably mounted to the first segment so as to rotate around a second axis, whereby to provide a second degree of freedom;
a third segment mounted to the second segment; and
a fourth segment movably mounted to the third segment so as to rotate around a third axis, whereby to provide a third degree of freedom, the fourth segment having an endpoint;
wherein the endpoint of the fourth segment of the first robotic device is configured for attachment to the first endpoint of the first appendage of the user and the fourth segment of the first robotic device is configured to be free of attachment to the first appendage segment of the user;

wherein the second endpoint of the fourth segment of the second robotic device is configured for attachment to the second endpoint of the second appendage of the user and the fourth segment of the second robotic device is configured to be free of attachment to the second appendage segment of the user; and wherein the first robotic device and the second robotic device are paired so that the first robotic device and the second robotic device move in conjunction with one another;

wherein the first axis of the first robotic device and the first axis of the second robotic device are disposed substantially horizontal, the second axis of the first robotic device and the second axis of the second robotic device are disposed orthogonal to the first axis of the first robotic device and the first axis of the second robotic device, respectively, and the third axis of the first robotic device and the third axis of the second robotic device are disposed parallel to the second axis of the first robotic device and the second axis of the second robotic device, respectively; and wherein, when the endpoint of the fourth segment of the first robotic device is attached to the first endpoint of the appendage of the user, and when the endpoint of the fourth segment of the second robotic device is attached to the second endpoint of the second appendage of the user, the first segment, the second segment, the third segment and the fourth segment of both the first robotic device and the second robotic device move during movement of the first and second appendages of the user, respectively, and none of the first axis, the second axis, and the third axis of either the first robotic device or the second robotic device are disposed coaxial with either the first joint or the second joint of either the first or second appendages of the user;

positioning the base behind, and to the side of, the torso of the user;
connecting a first appendage of a user to the endpoint of the fourth segment of the first robotic device and connecting a second appendage of a user to the endpoint of the fourth segment of the second robotic device; and
when a user moves the first appendage, causing the second robotic device to move the second appendage of the user.

14. A method for operating a robotic device in association a body of a user, wherein the body of the user comprises a torso and an appendage, wherein the appendage of the user has an endpoint, an appendage segment, a first joint movably connecting the endpoint to the appendage segment, and a second joint movably connecting the appendage segment to the torso of the user, the method comprising:
providing a robotic device comprising:
a base having a fixed configuration, the base being configured for disposition behind, and to the side of, the torso of the user;
a first segment movably mounted to the base so as to rotate around a first axis, whereby to provide a first degree of freedom;
a second segment movably mounted to the first segment so as to rotate around a second axis, whereby to provide a second degree of freedom;

a third segment mounted to the second segment; and a fourth segment movably mounted to the third segment so as to rotate around a third axis, whereby to provide a third degree of freedom, the fourth segment having an endpoint, the endpoint of the fourth segment being configured for attachment to the endpoint of the appendage of the user and the fourth segment being configured to be free of attachment to the appendage segment of the user;

wherein the first axis is disposed substantially horizontal, the second axis is disposed orthogonal to the first axis, and the third axis is disposed parallel to the second axis; and wherein, when the endpoint of the fourth segment is attached to the endpoint of the appendage of the user, the first segment, the second segment, the third segment and the fourth segment move during movement of the appendage of the user, and none of the first axis, the second axis, and the third axis are disposed coaxial with either the first joint or the second joint of the appendage of the user;

positioning the base behind, and to the side of, the torso of the user so that the reference frame of the robotic device is oriented similarly to the reference frame of the user, and attaching the endpoint of the appendage of the user to the endpoint of the fourth segment of the robotic device and leaving the appendage segment of the user free of attachment to the fourth segment of the robotic device; and moving at least one of the endpoint of the appendage of the user and the endpoint of the fourth segment of the robotic device.

15. A robotic device for operation in association with a user, wherein the user has a torso and a limb, and further wherein the limb comprises a plurality of segments connected together by joints, the robotic device comprising:

a base; and a robotic arm comprising a first end connected to the base and a second end terminating in an endpoint, wherein the base is configured for disposition behind, and to the side of, the torso of the user, and further wherein the endpoint is configured for attachment to a segment of the limb of the user;

wherein the robotic arm comprises a plurality of segments connected together by powered joints;

wherein, when the endpoint of the robotic arm is attached to a segment of the limb of a user, the powered joints move during movement of the limb of the user, and none of the powered joints is disposed coaxial with the joints of the limb of the user; and wherein the robotic arm comprises no more than four powered joints.

16. A method for operating a robotic device in association with a body of a user, wherein the body of the user comprises a torso and a limb, and further wherein the limb comprises a plurality of segments connected together by joints, the method comprising:

providing a robotic device comprising:

a base; and a robotic arm comprising a first end connected to the base and a second end terminating in an endpoint, wherein the base is configured for disposition behind, and to the side of, the torso of the user, and further wherein the endpoint is configured for attachment to a segment of the limb of the user;

wherein the robotic arm comprises a plurality of segments connected together by powered joints;

wherein, when the endpoint of the robotic arm is attached to a segment of the limb of a user, the powered joints move during movement of the limb of the user, and none of the powered joints is disposed coaxial with the joints of the limb of the user; and wherein the robotic arm comprises no more than four powered joints;

positioning the base behind, and to the side of, the torso of the user so that the reference frame of the robotic device is oriented similarly to the reference frame of the user, and attaching a segment of the limb of the user to the endpoint of the robotic arm; and moving at least one of the limb of the user and the endpoint of the robotic arm.

\* \* \* \* \*